United States Patent [19]
Davis

[11] Patent Number: 6,073,291
[45] Date of Patent: Jun. 13, 2000

[54] INFLATABLE MEDICAL PATIENT TRANSFER APPARATUS

[76] Inventor: David T. Davis, 537 Turner St., Bethlehem, Pa. 18018

[21] Appl. No.: 08/804,302

[22] Filed: Feb. 21, 1997

[51] Int. Cl.[7] .................................. A61G 7/10; B65G 7/06
[52] U.S. Cl. .................................. 5/711; 5/81.1 R; 5/706; 5/713; 5/715; 414/676
[58] Field of Search .................................. 5/81.1 R, 706, 5/710, 711, 712, 713, 714, 715, 731, 732, 739, 740, 652.1, 652.2, 654, 655.3, 655.9, 657.5, 914, 945; 180/124, 125; 414/676

[56] References Cited

U.S. PATENT DOCUMENTS

| | | | |
|---|---|---|---|
| 1,970,502 | 8/1934 | Hamza | 5/712 |
| 3,477,071 | 11/1969 | Emerson | 5/715 X |
| 3,775,781 | 12/1973 | Bruno et al. | 5/715 X |
| 3,790,975 | 2/1974 | Philipp et al. | 5/711 |
| 4,155,421 | 5/1979 | Johnson et al. | 414/676 X |
| 4,225,989 | 10/1980 | Corbett et al. | 5/714 X |
| 4,517,690 | 5/1985 | Wegener | 5/81.1 R |
| 4,627,426 | 12/1986 | Wegener et al. | 5/922 X |
| 4,629,162 | 12/1986 | Porché | 5/81.1 R |
| 4,686,719 | 8/1987 | Johnson et al. | 5/81.1 R |
| 4,843,663 | 7/1989 | Horvat et al. | 5/710 X |
| 4,962,552 | 10/1990 | Hasty | 5/713 |
| 4,977,629 | 12/1990 | Jones | 5/715 X |
| 5,044,030 | 9/1991 | Balaton | 5/654 X |
| 5,065,464 | 11/1991 | Blanchard et al. | 414/676 X |
| 5,375,273 | 12/1994 | Bodine, Jr. et al. | 5/715 X |
| 5,483,709 | 1/1996 | Foster et al. | 5/81.1 R |
| 5,561,873 | 10/1996 | Weedling | 5/81.1 R X |
| 5,594,190 | 1/1997 | Malta | 5/655.3 X |
| 5,701,621 | 12/1997 | Landi et al. | 5/652.1 X |
| 5,740,573 | 4/1998 | Boyd | 5/711 |

*Primary Examiner*—Brian K. Green
*Assistant Examiner*—Robert G. Santos
*Attorney, Agent, or Firm*—Charles A. Wilkinson

[57] ABSTRACT

An improved inflatable medical patient transfer apparatus has a combination of transverse partition members and a raised perimeter section to reduce deleterious ballooning and uneven inflation as well as quick emergency deflation and provide additional security for a patient supported upon such transfer apparatus. Additional differentially inflatable patient rolling chambers are preferably supplied on the top of the transfer apparatus to provide assistance to medical personnel in beginning to roll patients reclining or lying upon the transfer apparatus particularly in a deflated condition on a hospital bed. An improved air inlet arrangement is also provided along with certain indicia upon the surface of the transfer apparatus to expedite use by hospital personnel.

41 Claims, 9 Drawing Sheets

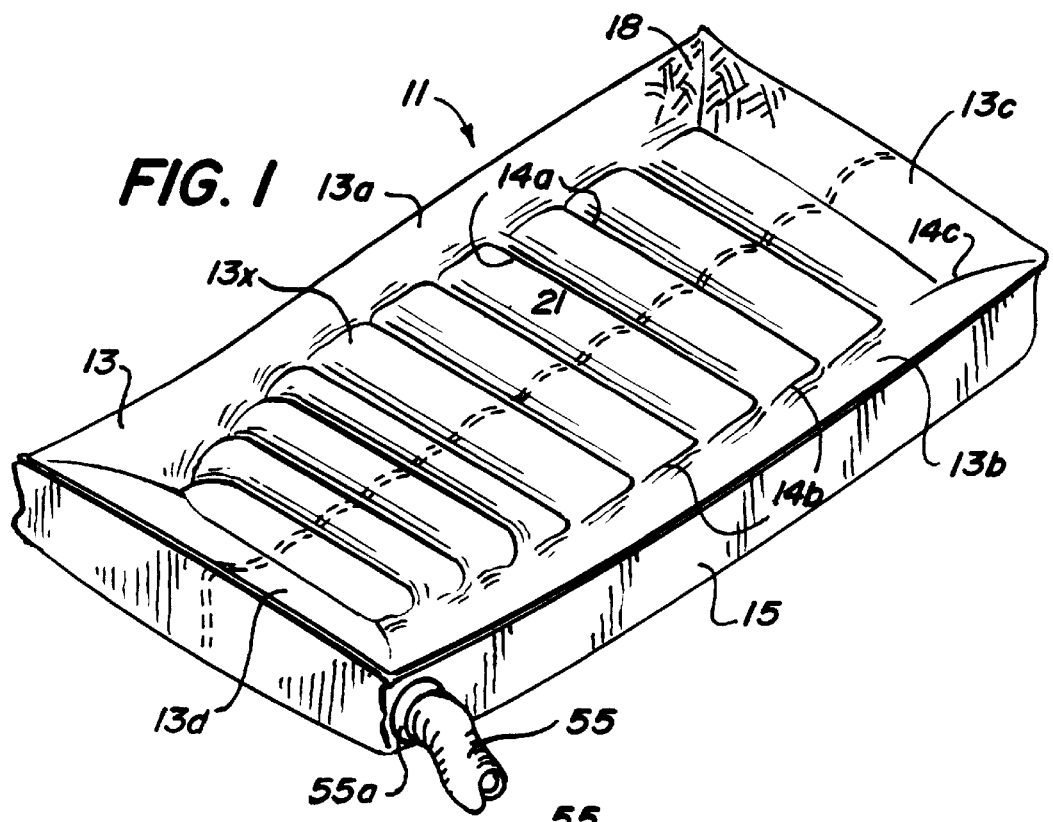
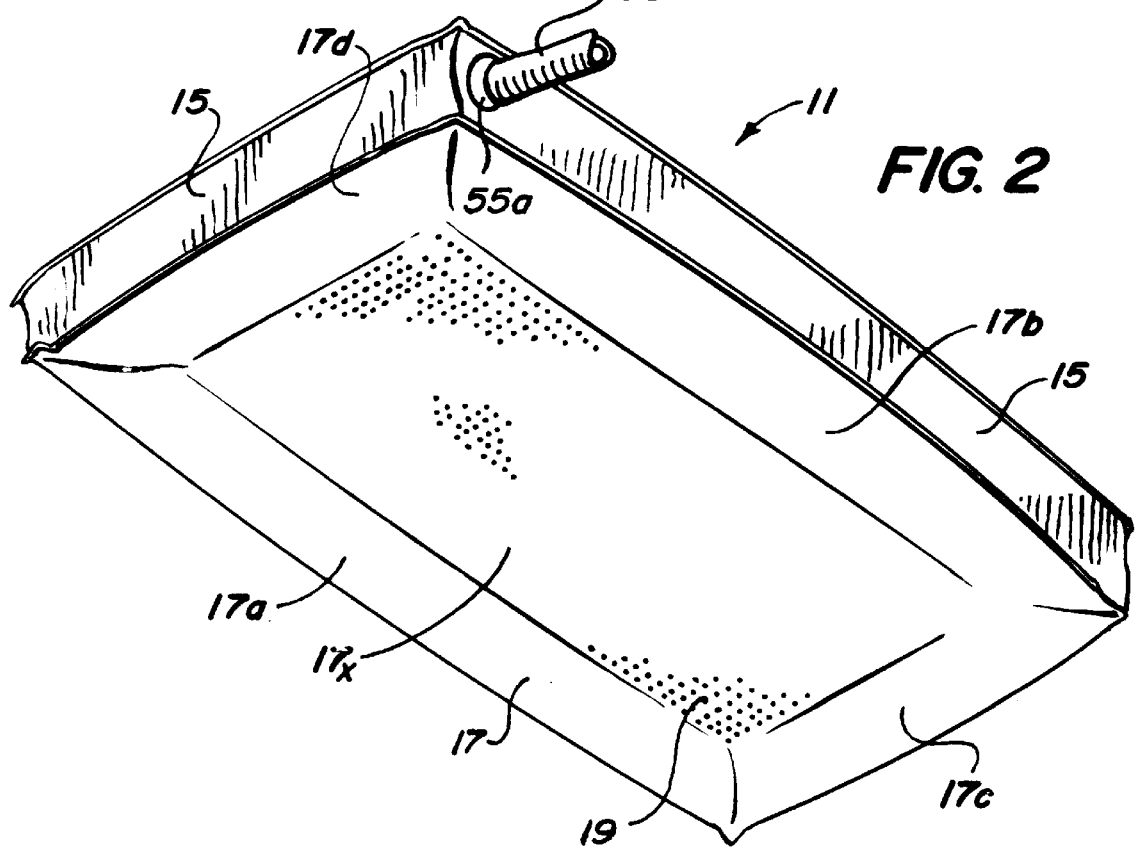

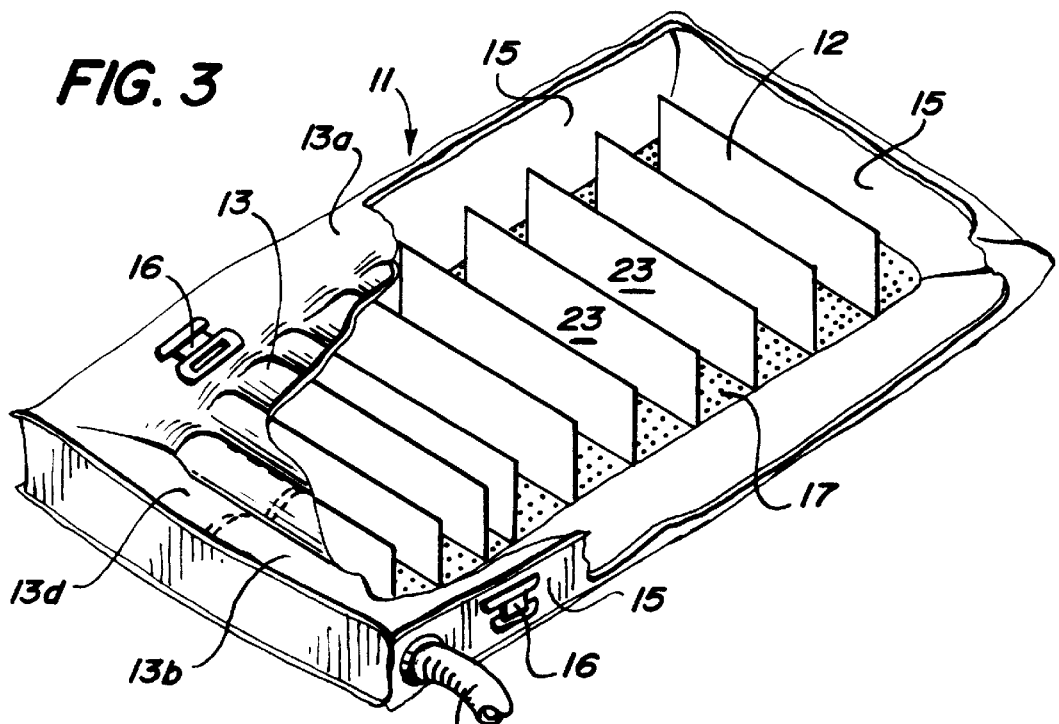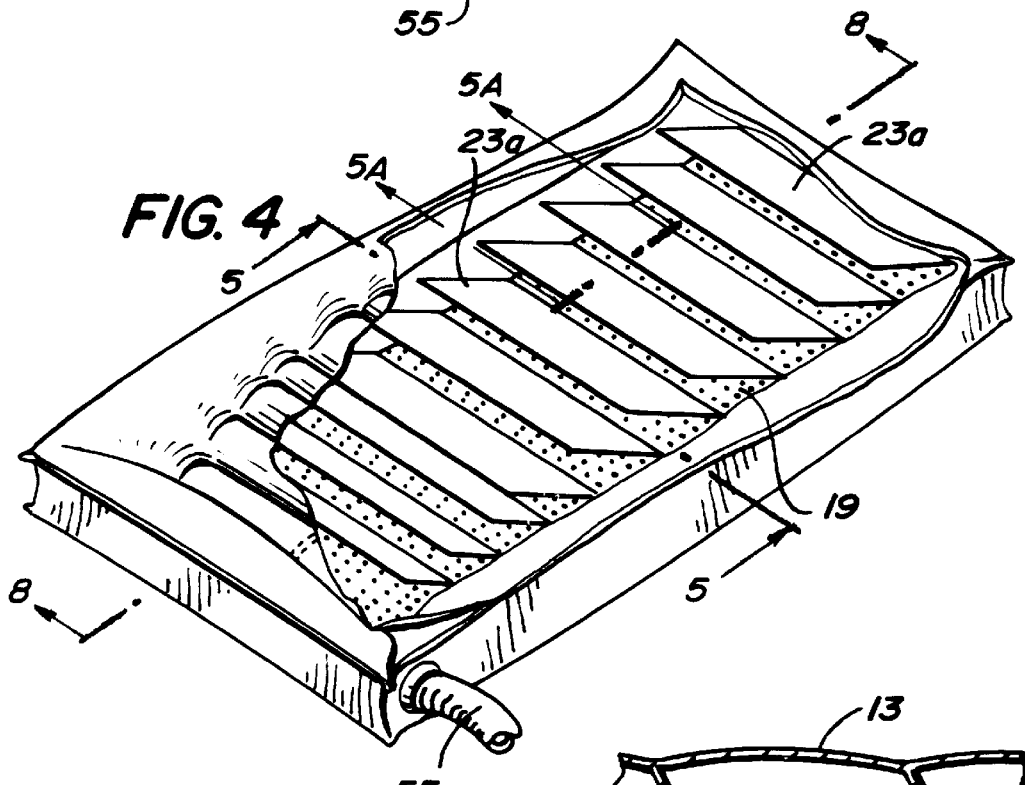

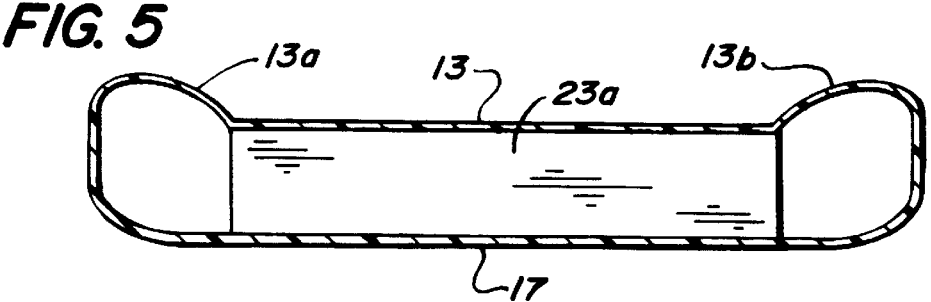
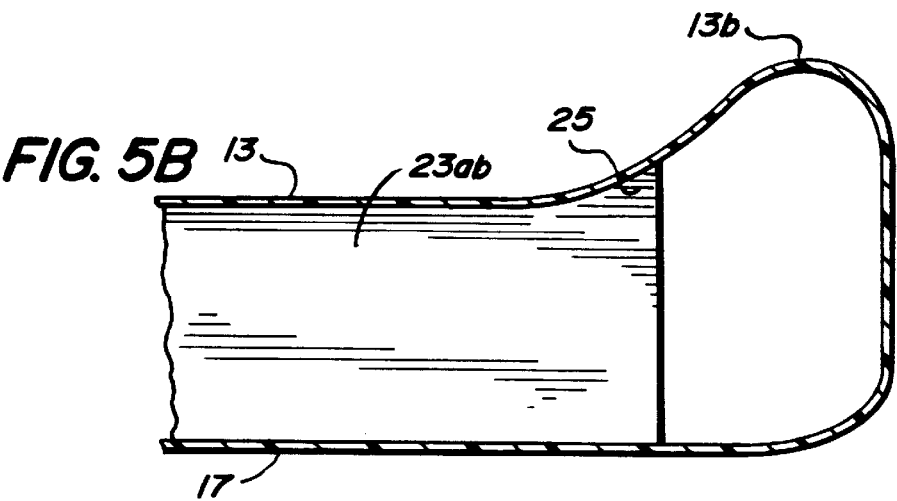
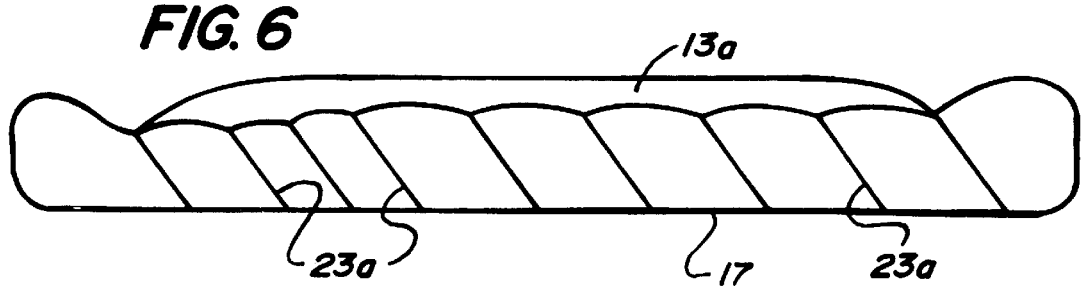
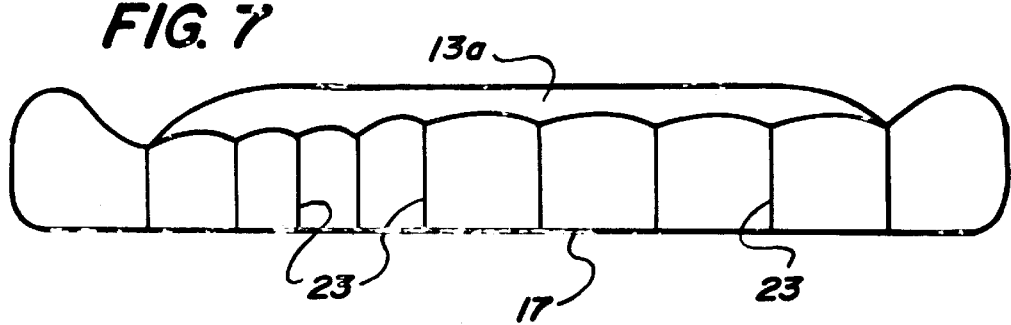

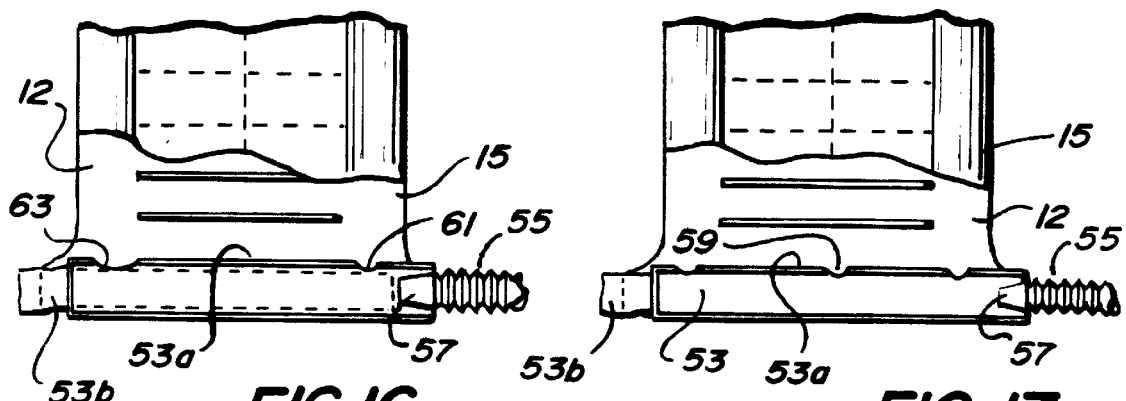
FIG. 16
FIG. 17
PRIOR ART
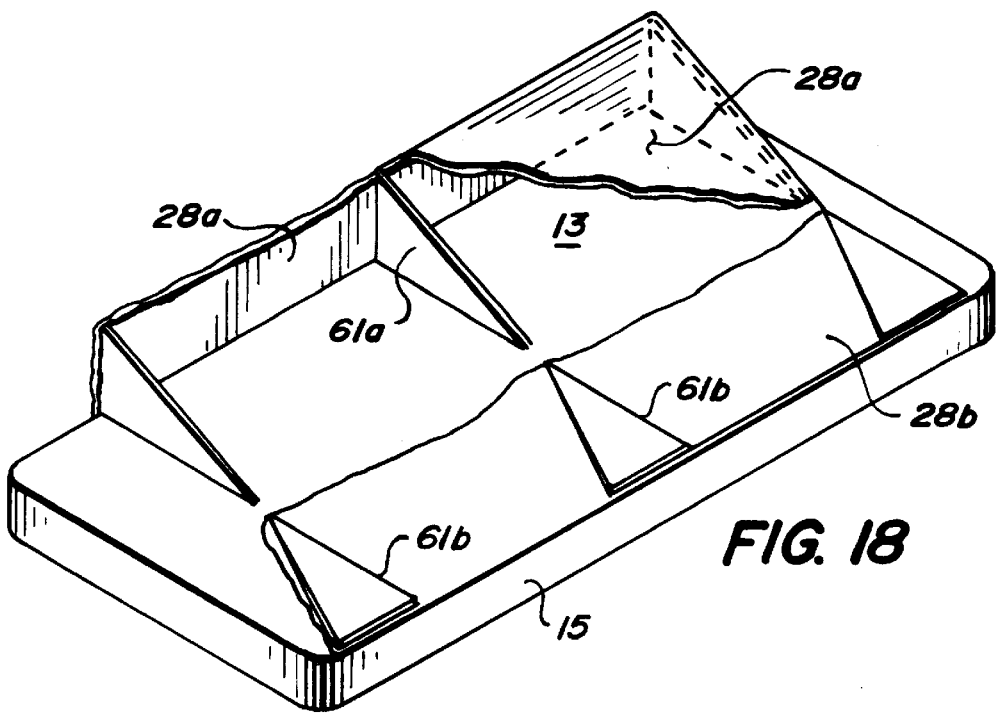
FIG. 18
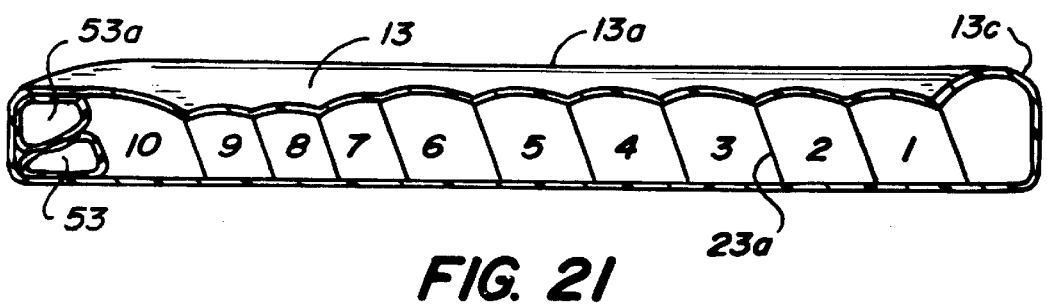
FIG. 21

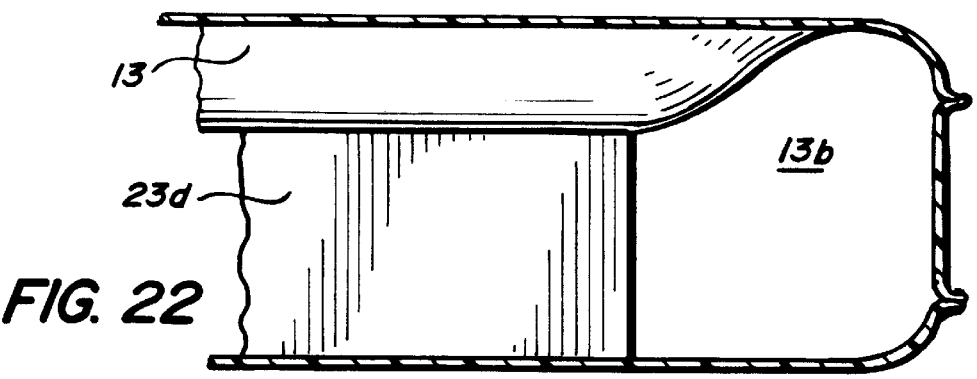
FIG. 22
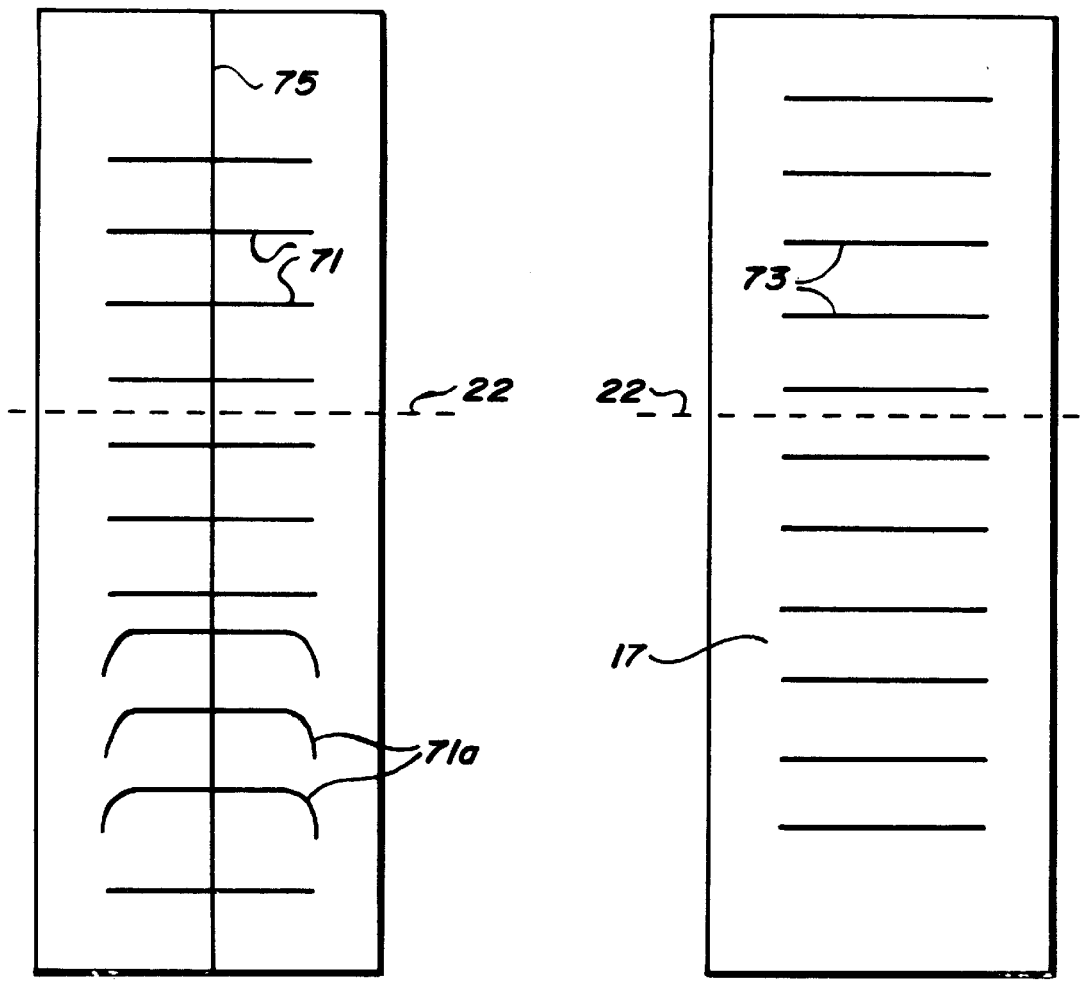
FIG. 19
FIG. 20 ly still, the invention relates to the use and structure of a
INFLATABLE MEDICAL PATIENT TRANSFER APPARATUS

BACKGROUND OF THE INVENTION

1. Field of the Invention

This invention relates generally to the transfer or transport of medical patients from one place to another within medical facilities as well as other locations and, more particularly, to air pallet or mat-type patient transfer apparatus for facilitating safe and comfortable support and transfer of medical patients from beds to gurneys or stretchers, or the reverse, particularly when the patient is to be transported or moved from one department or location in a hospital to another department or location in the same institution for various medical, surgical or diagnostic procedures. More particularly still, the invention relates to the use and structure of a semirigid air pallet in which one or more compressed air-filled chambers form a mat having a plurality of orifices in the bottom from which compressed air is released to support the mat slightly above the surface of beds, gurneys or the like or other surfaces allowing it to be moved in any direction desired over such surfaces.

2. Prior Art

Medical patients, including accident victims, the very elderly, comatose patients, patients paralyzed by strokes and other medical problems and the like, are frequently difficult to transfer or move in a safe, comfortable manner from one support surface such as a bed or the like to another support surface such as a gurney, or wheeled hospital cart, or the like, or from a stretcher or the like to a gurney, and finally, to a bed in a hospital or other medical facility. Patients who cannot sit up or move themselves are frequently particularly difficult to move from a stretcher to a bed or vice versa, frequently requiring two or three husky nurses or attendants with an ever present possibility of causing back injury and lost time to the medical personnel themselves, particularly if the patient is unusually heavy, as a disproportionate number of particularly troublesome or difficult to handle patients tend to be. In recent years, various transferrers or patient transfer or moving apparatus have been developed which can be placed either temporarily or semipermanently under a patient already on a bed or on a stretcher or the like and then inflated and moved onto another surface together with the patient. These transfer devices frequently take the form of air mattress-type movers. Such air mattress-type movers or transferrers have been provided with small perforations in the bottom plus a portable supply of compressed air to obtain and at least temporarily maintain inflation. During such inflation, a continuous supply of pressurized air is expelled from the bottom of the transfer device supporting the inflated transfer device or mat on any reasonably flat semicontinuous surface with a patient on top in the general manner of an air pallet sometimes used for industrial transportation within shops and plants.

Earlier examples of this general type of apparatus are, for example, disclosed in U.S. Pat. No. 3,948,344 entitled "LOW COST PLANAR AIR PALLET MATERIAL HANDLING SYSTEM", issued Apr. 6, 1976, and U.S. Pat. No. 4,272,856 entitled "DISPOSABLE AIR-BEARING PATIENT MOVER AND VALVE EMPLOYED THEREIN", issued Jun. 16, 1981, both of which used a low cubic foot per minute air flow which exited from a lower plenum chamber through a thin, flexible bottom sheet perforated by small, closely spaced pinholes over a surface area defined generally by the imprint or outline of the load, which pinholes during use would face an underlying, generally planar, support surface. The pinholes opened to the interior of the plenum chamber and ejected low pressure air directly upon a more or less planar support surface. Consequently, when the plenum chamber was filled or pressurized by low pressure air, such air would be initially blocked from passing through the orifices by the barrier presented by the planar surface upon which the air pallet rested. However as such air pressure increased, such pressure would lift or jack the load upwardly above the thin, perforated, flexible sheet as the pallet or patient mover inflated. Then, when the pallet or mover was completely inflated, the pressure therein would increase until the air began to escape under pressure through the minute pinholes, thereby creating a thin, frictionless air bearing between the underlying support surface and the bottom of the perforated flexible sheet upon which air bearing the air pallet plus any load or patient resting thereupon could be slid in any direction in which the air pallet was urged by a lateral force.

In all air pallets, including transfer devices for medical patients, it is necessary to provide a controlled pillowing or flexibility of the thin, flexible sheet material of the pallet, particularly beyond the perforated surface area of the sheet in order to initially jack the load above the flexible perforated bottom sheet prior to the creation of the frictionless air bearing by excess internal pressure as well as to insure the ability of the air pallet to ride over surface projections on the underlying support surface which may cause upward localized movement of the thin perforated bottom sheet. However, some means must also be provided within the air pallet to prevent ballooning of the unperforated top sheet as well as the thin, flexible perforated bottom sheet defining the plenum chamber. Otherwise, the plenum chamber would tend to expand vertically toward the ultimate assumption of a circular or near circular vertical cross section, the result of which vertical expansion would be loss of contact of substantial portions of the bottom sheet with the underlying surface and tilting or rolling of the load off the top of the air pallet. In addition, when the load rests on the air pallet prior to the pressurization of the plenum chamber, the load tends to press the perforated flexible sheet into contact with the underlying support surface and the upper sheet into contact with the bottom sheet which prevents the entry of air under light pressure into the plenum chamber. Consequently, it has been found that some form of dispersion means are usually required either interiorly or exteriorly of the plenum chamber to ensure proper pressurization of the plenum chamber.

Under certain circumstances, the load itself may constitute a generally rigid or semirigid backing member. For example, in the case of a cardboard box filled with material for transport, the bottom of the box may have the planar bottom function as a generally rigid backing member preventing either the upper or lower flexible sheet from ballooning so long as the internal pressure does not become too high. Even a fairly large bag of grain superimposed as the load may serve as an effective generally rigid backing member to prevent ballooning of an underlying support pallet. In the case of a human body, such as that of a medical patient, resting on the thin upper surface of a patient mover, however, the load is neither flat nor rigid and the top of the pallet will merely tend to inflate on one side or the other of the patient's body and progressively roll such patient off the side of the pallet. Meanwhile, inflation or ballooning of the bottom of the pallet will likewise cause the bottom of the entire pallet to tend to assume an arcuate configuration and as a result rock to the side aiding in rolling the patient off onto the floor or other underlying surface.

In the early development of air bearing patient movers as exemplified by U.S. Pat. No. 3,948,344, a corrugated sheet placed within the single chamber of the mat functioning as a plenum chamber prevented ballooning of the two superimposed thin, flexible sheets by opposing decrease of lateral dimensions. In U.S. Pat. No. 4,272,856 a more or less rigid member constitutes both a unitary air dispersion medium and a semirigid backing member. The semirigid backing member might comprise a semirigid sheet inserted within a cavity formed between the top thin, flexible sheet and an intermediate thin, flexible sheet. Alternatively, the backing member might, in certain later constructions, be formed of a series of transversely-linked, air-pressurized tubes formed by sealing off parallel, laterally-adjacent, longitudinal sections of the top sheet and an intermediate sheet. Such tubes might be completely sealed and air pressurized through valves. In a flow-through system, on the other hand, the pressurized air forming the air bearing passes first through the parallel, transversely-linked tubes defined by the top and intermediate sheets, and then into a separate lower plenum chamber defined by the intermediate sheet and the bottom sheet with the bottom sheet having a series of perforations, the pattern of perforations usually being confined to the outline or footprint of the load. U.S. Pat. No. 4,528,704 issued to Jack Wegener and Raynor D. Johnson, on Jul. 16, 1985 and entitled "SEMI-RIGID, AIR PALLET-TYPE PATIENT MOVER" is directed to air pallets of this general nature.

U.S. Pat. No. 4,417,639 issued to Jack Wegener on Nov. 29, 1983, and entitled "DYNAMIC GAS PRESSURIZED JACKING STRUCTURE WITH IMPROVED LOAD STABILITY AND AIR PALLET EMPLOYING SAME," on the other hand, discloses a flow-through chamber connected by succeedingly smaller sized ports within a series of horizontally extending vertically spaced walls forming a series of stacked chambers in the form of a gas-pressurized jacking structure and an air pallet including such jacking structure. FIG. 10 of such patent shows a jacking structure formed totally of thin, flexible sheet material with vertically separated chambers in communication via a gas passage whose cross-sectional area is smaller than that of the air inlet to the upper chamber.

U.S. Pat. No. 4,686,719 entitled "SEMI-RIGID AIR PALLET-TYPE PATIENT MOVER", discloses a semirigid, air pallet-type patient mover having U-straps sewn to the lateral sides of the mover structure for facilitating lateral shifting of the patient placed thereon while the plenum chamber is pressurized and a thin-air film underlying the perforated area of the thin, flexible bottom sheet provides an air bearing. The patient may be bound to the top of the patient mover via a pair of crossed VELCRO hook-and-loop material-covered straps for ease in engagement and disengagement of the strap ends about the patient.

Air pallets and particularly patient mover type-pallets, which are usually formed of multiple, thermal bonded or stitched sheets of thin, flexible sheet material have in the past, as explained above, frequently incorporated a rigid or a semirigid sheet as the load-backing member. However, such a construction has not been universally employed in health care treatment facilities. The existence of the rigid or semirigid sheet carried within a pocket or cavity defined by two thin, flexible sheets renders the assembly bulky, and adds considerably to the weight. The lack of flexibility may also prevent passage of the transfer devices or patient movers through narrow passages. While such patient movers may perform extremely well at discrete hospital treatment stations or treatment areas such as, for example, where the patient mover may be used for facilitating patient movement onto and from an X-ray table, the patient mover tends to remain at its primary area and is unlikely to be employed in moving the patient to and from hospital beds remote from the X-ray area, since hospital personnel tend to resist transporting such a patient mover from location to location.

The same is true where air pallets in the form of patient movers are utilized by paramedics, shock trauma units or the like. As a result, there has more recently been considerable interest in the development of soft pad or hard pad air chamber-type air pallets as patient movers or as patient positioners. In the health care field, the person moved or whose position is being changed may not in many cases be truly a patient recovering from sickness, but a person requiring continuous attention, such as an invalid or partial invalid. In this case, upon either transport, or positioning and maintaining the patient comfortable in a given partially upright or supine position, there is a distinct possibility of a tissue breakdown if the patient remains in such given positions for significant periods of time. In general, a flexible patient mover causes less tissue breakdown of this nature than a rigid patient mover.

Successful operation of a rigid backing surface-type air pallet requires (a) controlled jacking, (b) controlled pillowing and (c) anti-ballooning. Control of load distribution may be achieved by the use of a rigid backing member such as a board or sheet as part of the plenum chamber, or within a separate chamber supporting the load, but overlying the plenum chamber. The rigid backing member distributes the load mass balanced equally over the area of the plenum chamber footprint. The control of the plenum chamber can also be performed in several other ways and a properly designed plenum chamber can effect several of the control functions, i.e., regulation of jacking, pillowing and ballooning.

Where, for example, the thin, flexible bottom sheet is tightly connected at opposite sides to a generally rigid backing member, such rigid backing member itself will function to control jacking, pillowing and ballooning. Where the rigid backing member is smaller than the thin, flexible bottom sheet, however, slack develops within the thin, flexible bottom sheet and such slack increases the pillowing capability of the thin, flexible bottom sheet. Excessive slack leads ultimately, however, to ballooning.

Other means have in the past been provided for controlling pillowing, such as the lamination of additional members to a center sheet or to either the upper thin, flexible sheet or the bottom thin, flexible sheet. The addition of internal strips lying diagonally from corner to corner within the plenum chamber or vertical from face to face have also been used to control the degree of pillowing. The load itself, as explained above, may act as a pillowing control means. The insertion of a rigid plate internally within a thin, flexible bag may act both as a rigid backing member, a pillowing control means and, under certain conditions, an air distribution means for insuring air pressurization of the plenum chamber with the air pallet formed principally by the bag supporting the load prior to air pressurization of that plenum chamber. The size of the blower and thus the air pressure developed within the plenum chamber may serve to control pillowing, as may valving or gating of the air flow system entering the plenum chamber and creating the air bearing, and the stiffness or flexibility of the material used in forming the thin, flexible bottom sheet. The area of the material around the perforation pattern and between that pattern and the rigid backing member is normally the primary pillowing control means for such air pallets. The proximity of the perforation pattern to the outside edge of the plenum chamber, the slack in the plenum chamber and the rigidity of the backing member all may constitute aspects of the pillowing control.

In U.S. Pat. No. 4,272,856 directed to an air pallet-type patient mover, pillowing is controlled by having the pattern of perforations extending to the edge of the plenum chamber and the sides of the plenum chamber are purposely designed to match the head and torso of the patient from the shoulders to the hip, where the load mass of the patient is concentrated. Certain parameters with respect to the load, i.e. weight, patient size and load footprint, are matched to the plenum chamber area, otherwise the unit will not work or work poorly.

As disclosed in U.S. Pat. No. 5,561,873, it was ascertained that an air pallet plenum chamber, upon pressurization, tends to take a shape resulting in lateral reduction of the plenum chamber air-film footprint. Since the patient's body is movable and flexes, this creates significant problems. Not only is such load not rigid, but the top flexible sheet is not a rigid member. Further, only the torso and head are supported or jacked up by the plenum chamber and the rest of the body such as the legs and arms are simply carried along with the air pallet once an air bearing or air film is created by escape of air through the perforations within the thin, flexible bottom sheet to support the torso and head. Patient loading on the air pallet and removal from the air pallet also produce significant problems. Thus, the ability to create a patient mover having a size which will fit the patient, a bed, a portable gurney and a procedure table such as an operating table was recognized as being quite desirable.

These problems led initially to developments disclosed in U.S. Pat. Nos. 4,528,704 and 4,686,719. However, these developments raised other problems. The key to solving most of the problem areas seemed to lie in the utilization of a rigid backing member, but a rigid backing member made it more difficult to place the patient on the patient mover. The patient has, in such arrangements, to be physically log rolled to one side, frequently to almost a facedown position to one side so that the rigid backing member is juxtapositioned to the patient, and the patient is then rolled back over so that the patient ends up supine on the patient mover. This procedure is basically similar to placing a sheet under a patient when on a hospital bed. In such procedure, however, the sheet is usually folded in half and slid under the patient without turning his or her body excessively to one side. A rigid backing member prevented the use of such a folding procedure, however. It also restricted passage of the patient mover through passageways of restricted dimensions.

Attempts were thus made to eliminate the rigid backing member. At the same time, the separation of the jacking action from that of creation of the frictionless air film was sought. This led to the development of stacked tubes, one functioning as a pure jacking member, and the second as a combined jacking chamber and plenum chamber from which the air bearing is derived. The result was a gas pressurized jacking structure with improved load stability, in which the same compressed air pressurizing the upper chamber through a dynamic flow-through arrangement, functioned also to inflate the plenum chamber and in passing through the orifices in the thin, flexible bottom sheet, to create the air film or air bearing under the air pallet-type patient mover.

However, in such air chamber-type air patient movers, upon air pressurization of the tubular chambers formed by sealed sections of the upper two thin, flexible sheets and the air pressurization of the plenum chamber underlying all of the upper row of tubes common to the intermediate thin, flexible sheet of said row of tubes, the entire unit tended to take on a circular or cylindrical cross section. This phenomenon was termed "hot dogging". During "hot dogging," the plenum chamber tends to take on an almost circular cross section in a plane at right angles to the longitudinal axis of the series of joined tubes formed by the top thin, flexible sheet, the intermediate thin, flexible sheet and the bottom thin, flexible sheet of the air pallet. A plenum chamber is formed between the thin, flexible intermediate sheet and bottom sheet with the bottom sheet having literally thousands of closely-spaced pinholes through which air escapes from the plenum chamber to form an air film or air bearing between the thin, flexible bottom sheet and the generally rigid, planar surface beneath. Each of the transverse seal lines joining the top and intermediate sheets, which seal lines together form individual air pressurizable chambers or separate tubes, function as hinging areas allowing relative arcuate movement between adjacent tubes. The result of such hinging is a very high instability for any load in contact with the exterior of the top thin, flexible sheet forming the top of the patient mover. Furthermore, the single large sectional area formed by the plenum chamber at the bottom was not able to control the "hot dogging" and the entire air pallet patient mover was thus extremely susceptible to instability with respect to any load.

The "hot dogging" also resulted, under severe conditions, in a loss or reduction in effective air film or air-bearing, cross-sectional area which, when it becomes too small to carry the load, causes the air bearing to become inoperative. In addition, the load, or patient, might roll off the upper flexible sheet support area as the air pallet assumed a cylindrical shape and the air pallet might ground out, i.e. portions of the intermediate sheet might contact the bottom perforated sheet forcing it against the underlying supporting surface and destroying mobility, as air bearing cross-sectional area is lost. A combination of all three adverse effects might easily occur.

The phenomenon of hinging between adjacent chambers of air chamber-type air pallets using discrete separate air chambers also results in a lack of rigidity of the air chamber assembly defined by a top thin, flexible sheet and an intermediate thin, flexible sheet. As a result of separate air pressurization of each of the chambers of the upper row of tubes and the air pressurization of the lower plenum chamber, which underlies the tube array defined by the top and intermediate thin, flexible sheets, instability of the lower plenum chamber is accentuated. While the walls of the individual chambers or tubes are relatively taut, upon air pressurization, the line connections between abutting sides of the parallel row of tubes permit tube sectioning lines to act as hinges which may cause unwanted hot dogging of the air pallet as well as other overall shape instability. The presence of a load such as a patient and the weight of said patient depressing the upper surface of the air pallet tends to resist the ballooning of the air pallet and enhance the stability of the load. However, the structures inherently lack means for preventing significant lateral shrinking of the plenum chamber and other shape instabilities.

As disclosed in U.S. Pat. No. 5,561,873, an investigation of the various causes for non-rigidity in contrast to desired rigidity when attempting to substitute an air chamber or chambers for a rigid backing member led to the determination that rigidity of any part of an air chamber-type air pallet can be achieved from solely two means: (a) careful control of the air pressure within the various chambers of the air pallet, particularly with respect to control of overly high air pressure found to be undesirable due to potential ballooning, and (b) employing a solid unbendable stiff upper sheet to support the load which, for a given point or area load, spreads such load over the complete surface of the unbendable upper sheet. While the unbendable upper sheet was sufficient to provide rigidity and avoid ballooning in at least one embodiment of U.S. Pat. No. 4,528,704, the necessary rigidity can only come from the air pressure within, or, more correctly, flowing through the various chambers of the thin, flexible sheet structure.

In operation of air chamber-type air pallets of the design of U.S. Pat. No. 4,528,704, the plenum chamber being unsectionalized and linked solely to the tubular arrays at opposite ends and along opposite sides of the air pallet, such structure either creates, or enhances, non-rigidity of the structure which prevents the row of tubes of said air pallet from successfully acting as a substitute for the rigid backing member normally employed in such air pallet structures. This results in hinging between the inflated tubes, fostering ballooning of the structure, and creating instability.

In U.S. Pat. No. 5,067,189, entitled "AIR CHAMBER-TYPE PATIENT MOVER AIR PALLET WITH MULTIPLE CONTROL FEATURES", issued Nov. 26, 1991, the foregoing described problems of over pressurization causing instability of the patient mover and the load, enlargement of the underlying plenum chamber to an almost vertical circular cross section, i.e. "hot dogging", during pressurization, the requirement for a rigid or semirigid backing member to prevent "hinging" between individual longitudinal chambers or tubes for supporting the load, and the point load grounding out on the underlying support surface due to load shifting were tentatively resolved. During the course of improving the earlier air pallet patient movers of the air chamber type, it was found that all of the recited problems with prior types of inflatable air pallets were substantially interrelated, as well as the discovery of an additional structural problem described as the reduction or shrinkage of the lateral dimension of the air pallet. U.S. Pat. No. 5,067,189 reduces the recited problems through a novel interrelated structure. In lieu of a rigid or semirigid backing member, a series of stacked rows of pressurized chambers or tubes are utilized to create a predetermined air dispersion which, in concert with the air dispersion in the underlying plenum chamber, properly jacked the load, e.g. a patient, and maintains the flexible backing surface (the stacked rows of tubes or chambers) in a planar direction generally parallel to the underlying developed air film. Simultaneously, the plenum chamber is inflated and through the underlying perforations, creates an air film between the air pallet and the fixed support surface, but only in an area which generally matches the footprint of the load. Further, the inflation of the plenum chamber within the parameters set forth in U.S. Pat. No. 5,067,189 creates a sufficient pillowing means to permit the air pallet to accommodate surface irregularities and move the load on the developed air film without bottoming out and without the bottom flexible sheet ballooning outward. This is accomplished through a series of vertical and oblique ties which restrain the separation of an intermediate sheet forming the bottom of the linked rows of chambers or tubes and the underlying bottom sheet of the plenum chamber from moving outward one from the other beyond a predetermined distance or dimensions. These ties (or stringers) in combination with the stacked rows of chambers or tubes, prevent "hot dogging" of the air pallet when inflated, tends to reduce lateral shrinkage of the air pallet because of its "anti-hot dogging" and anti-ballooning effect, and increase the ability of the air pallet to accommodate surface irregularities when in motion so as not to create a point load problem, all of which increase the load stability of the particular air pallet.

The invention disclosed in U.S. Pat. No. 5,561,873 entitled "AIR CHAMBER-TYPE PATIENT AIR PALLET WITH MULTIPLE CONTROL FEATURES" improves upon the inventions of the U.S. Pat. No. 5,067,189 patent by providing between a top sheet and bottom or intermediate sheet, a more or less rectangular array of centrally positioned chambers laterally oriented and separated from each other by a series of substantially vertical walls comprised of lateral and longitudinal partition members or walls secured to the top and bottom sheets, or in some embodiments where a separate bottom planar chamber, or plenum chamber, is used, an intermediate sheet. The lateral and longitudinal partition members are secured to the top and bottom or intermediate sheets by sewing, thermal welding or the like and essentially serve to prevent the top sheet and underlying sheets from expanding too far from each other, which effectively prevents "ballooning" and so-called "hot dogging" yet allows effective "jacking" and "pillowing" at the same time achieving effective stability and preventing both lateral and longitudinal shrinkage. Essentially free passage of pressurized air is allowed between the various laterally-oriented central chambers and a peripheral chamber extending completely around the rectangular array of central chambers. As disclosed in the patent, the combination of the central array of lateral chambers and securing of the lateral and longitudinal partition members to the top and bottom or intermediate sheets in the center, prevents ballooning and hot dogging, together with the lateral and longitudinal shortening occasioned by ballooning as the result of the vertical expansion occasioned by ballooning. Also, because of the way the lateral and longitudinal partition members are combined, a very strong tacked or secured structure which has little tendency to stress tearing of the sewing or heat welding lines, is provided. Two types of lateral and longitudinal partition members are disclosed, one of which makes use of separate members with the longitudinal members disposed at the ends of the transverse chambers formed by the lateral partition members and the other in which the longitudinal partition members are discontinuous as the result of being formed by a right-angled turn of the lateral partition members plus an opening at the end to allow free circulation of gas or low cubic foot per minute air throughout the structure.

When the longitudinal partition members are not discontinuous, they have orifices provided in them and are preferably tacked to the top and bottom or intermediate sheets slightly beyond the ends of the lateral partition members to allow free circulation of pressurized air between the various lateral chambers of the rectangular array of chambers as well as with the outer peripheral rectangular chamber. The lateral partition members may be secured within the rectangular array of chambers in an inclined orientation to facilitate lying down of such partition members uniformly in a deflated position.

While the invention of the U.S. Pat. No. 5,561,873 patent has been quite successful and has solved major problems previously existing in medical patient transfer devices and the like, there is room for improvement, some of which improvements are provided by the present invention.

Perforated upper sheets have also been used in hospital environments to provide so-called "low air loss" type arrangements in which low pressure air is blown upwardly against a patient reclining upon the apparatus, not to lift the patient, but to essentially prevent the skin of the patient from becoming too moist and breaking down into bed sores and the like. This type of air loss apparatus is also used in connection with burn patients.

OBJECTS OF THE INVENTION

It is an object of the invention, therefore, to provide an improved inflatable medical patient support and transfer apparatus providing superior circulation and access of pressurized air to all portions of the apparatus instantaneously in order to prevent any initial unevenness of inflation with possible resulting instability.

It is a further object of the invention to provide an improved inflatable medical patient support and transfer apparatus in which all the internal partitions can be laid down uniformly in a deflated condition to eliminate folding causing lumps under the patient which could have deleterious consequences.

It is a still further object of the invention to provide an inflatable medical patient support and transfer apparatus which is radiologically shadow free.

It is a still further object of the invention to provide an improved inflatable medical patient support and transfer apparatus having upwardly raised sides to counteract any tendency of a patient to roll off the transfer apparatus.

It is a still further object of the invention to provide a very rapidly deflatable transfer apparatus adapted for emergency application of cardiopulmonary resuscitation, or C.P.R.

It is a still further object of the invention to provide a medical patient support having an effective means for aiding in rolling a patient one way or another from the surface of the transfer apparatus.

It is a still further object of the invention to enhance a feeling of security in a patient carried upon a medical patient support.

It is a still further object of the invention to provide a readily recognizable guide for medical personnel in distinguishing the proper side of an inflatable medical patient support to place the patient upon.

It is a still further object of the invention to provide a medical patient support and transfer apparatus that will, when required, urge a supported patient toward one side by raising the opposite side of the supporter and transfer apparatus.

It is a still further object of the invention to provide a medical patient support and transfer apparatus having additional inflatable chambers on the surface such that when desired, one side or the other may be raised to aid in rolling a patient supported by the inflatable transfer apparatus to a desired side of the transfer apparatus.

It is a still further object of the invention to provide an inflatable transfer apparatus which can be used as a semi-permanent covering for a hospital bed in a deflated condition, and can be used in such deflated condition to jack or raise a patient on one side to aid in changing the position of the patient.

It is a still further object of the invention to simplify the design of an inflatable patient transfer apparatus for more convenient manufacture.

It is a still further object of the invention to provide an inflatable transfer apparatus having reference indicia for centering or arranging a patient on such transfer apparatus.

It is a still further object of the invention to combine low air loss capability with such transfer apparatus.

Further objects and advantages will become evident upon review of the following detailed description and discussion together with the appended drawings

BRIEF DESCRIPTION OF THE INVENTION

An improved inflatable patient support and transfer apparatus is provided having a smooth non-lumpy deflated surface as the result of elimination of any longitudinal partition members or structures and relying completely upon transverse partition members to define a substantially rectangular array of transverse chambers in the center of the patient support and transfer apparatus, which array serves to prevent over expansion and misshapening of the inflatable apparatus. Combined with the single mode partition members is a peripheral side member having increased vertical dimensions greater than the effective vertical dimensions of the transverse partition members which, in combination, provides an expanded outer peripheral chamber which serves to form a raised outer periphery to the inflatable structure providing additional security to a supported patient with respect to accidental rolling of such patient off the transfer apparatus. The expanded outer chamber also provides expanded air volume capacity providing enhanced rapidity and uniformity of flow of air into and from the central rectangular chamber patient support area and stiffening the entire transfer apparatus when inflated. The combined construction is such as to relieve stress from the interattachment of the transverse partition members and the top and bottom sheets so the overall construction is more durable and damage resistant than otherwise. The inflatable pad or transfer apparatus is also preferably provided with two additional inflatable top chambers for use primarily when the inflatable patient support and transfer apparatus is deflated under a patient upon a hospital bed and which, upon unitary inflation one at a time, serve to aid in rolling a patient's body to one side or the other of the inflatable structure. The two additional inflatable top chambers may also be used when the transfer apparatus as a whole is inflated. The top and bottom sheets of the apparatus should be color coded to easily differentiate from the bottom of the transfer apparatus with small gas orifices and the top of the apparatus upon which the inflatable roll chambers are located to prevent the patient from being placed upon the wrong side of such transfer apparatus, particularly when deflated. Reference indicia to indicate or define the center line of the apparatus for correctly aligning a patient upon the apparatus is provided. The raised periphery of the apparatus may be only disposed along the sides of the transfer apparatus instead of extending completely around the apparatus, but in such instance, it is preferred to arrange the ends of the apparatus such that an equal volume of air space is available at all points for movement of air around the periphery, particularly to accommodate even inflation without any tendency to unequal inflation or interference with substantially instantaneous emergency deflation. Low air loss arrangements for providing a soothing flow of low pressure air across the body of a patient is also provided.

BRIEF DESCRIPTION OF THE DRAWINGS

FIG. 1 is an isometric upper view of an inflatable support and transfer apparatus in accordance with the invention.

FIG. 2 is an isometric bottom view of the inflatable support and transfer apparatus of the invention shown in FIG. 1.

FIG. 3 is a partially broken away isometric view from the top of the apparatus shown in FIGS. 1 and 2.

FIG. 4 is a partially broken away isometric view from the top similar to FIG. 3 showing a preferred embodiment of the apparatus of the invention.

FIG. 5 is a transverse section through FIG. 4 showing one of the transverse partition members.

FIG. 5A is a partial longitudinal section through FIG. 4 showing several of the transverse chambers.

FIG. 5B is a partial transverse section through an improved embodiment of the invention.

FIG. 6 is a longitudinal section through a device similar to the transfer apparatus shown in FIG. 4, but having a peripheral chamber restricted in length along one side.

FIG. 7 is a longitudinal section through a device similar to that shown in FIG. 3, but having a peripheral chamber restricted in length along one side.

FIG. 16 is a diagrammatic partially broken away top view of an improved air inlet to one of the transfer devices in accordance with the invention.

FIG. 17 is a diagrammatic top view similar to FIG. 16 showing the prior art arrangement for inletting air to the transfer apparatus of the invention.

FIG. 18 is a partially broken away isometric view of the internal ribs of in the log rolling chambers at the top of a transfer device such as shown in FIGS. 10 through 15.

FIG. 19 is a diagrammatic top view of a successfully used commercial version of the invention.

FIG. 20 is a diagrammatic bottom view of the embodiment of the invention shown in FIG. 19.

FIG. 21 is a longitudinal section of the embodiment shown in FIGS. 19 and 20.

FIG. 22 is a partial transverse section of the embodiment of the invention shown in FIGS. 19 through 21.

DESCRIPTION OF THE PREFERRED EMBODIMENTS

Figure 8:
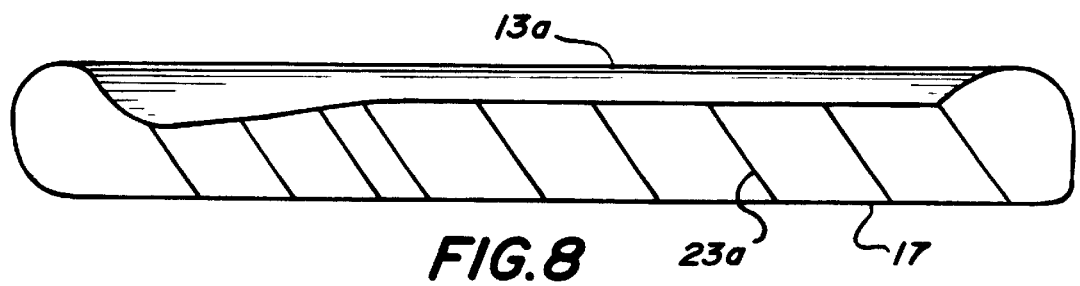
FIG. 8 is a longitudinal section through the preferred embodiment of the invention shown in FIG. 4.

It has been found that there are significant differences between a rigid support-type air pallet and a flexible or air chamber-type air pallet supporting a load that can flex such as, for example, a human body. Air pallets and air pallet-type patient movers utilizing a thin, flexible bottom sheet partially defining a plenum chamber and perforated with thousands of small closely spaced pinholes over the bottom surface area defined by the outline or footprint of the load have generally employed a rigid backing member starting with U.S. Pat. No. 3,948,344. However, the patient movers of the U.S. Pat. No. 4,272,856, and U.S. Pat. No. 4,528,704 particularly as illustrated in FIGS. 4 and 5 of such latter patent have used flexible constructions which have definite advantages in storage and movement through close quarters where it may be desired to flex the patient mover to secure easy passage.

Certain structural features and parameters play an important part in the successful operation of an air pallet incorporating a rigid backing member. The key for successful movement of a load of any type on an air film formed by air escaping from perforations in the pallet is to make the air work opposite to the weight of the load and to control the action of the air in so doing. By matching the footprint of the load to the configuration of orifices in the plenum chamber, an air pallet with a plenum chamber pressurized within it and orifices leading from such chamber will correctly jack the load, create a proper air bearing and permit the load to be stably moved on the air pallet.

If the mass of the load is spread over too small an area against the plenum chamber, i.e., point loading, the load may ground out a portion of the plenum chamber against the underlying planar support surface or may cause a portion of the lower thin, flexible sheet to bulge out around the point load application against the top of the plenum chamber. If the plenum chamber bulges up and about the sides of the load, the load is not lifted, the air does not escape through the perforations and no effective air bearing is created. When the load footprint is less than the plenum chamber air film footprint, therefore, a significantly greater pressure is needed to lift the load.

In the present context, the term "jacking" refers to initially raising the load so that air can enter into and be distributed throughout a plenum chamber, or multiple plenum chambers, and then pass out through perforations in the bottom of the plenum chamber to form an air film or air bearing to both support the load and allow it to move or be moved upon the film of air.

The term "pillowing" describes the ability of the thin, flexible sheet to deform so as to ride over surface irregularities in the generally planar support surface (ground, floor, etc.) without bottoming out. If the compressed air within the plenum chamber does not jack the load high enough, a rigid backing member or load on top of the air pallet will ground out against the thin, flexible bottom sheet and the surface irregularity (vertical projection) prevents further movement or interferes with such movement.

The term "ballooning" describes the situation where the load is jacked or raised up so high that the load becomes unbalanced on the footprint formed by the plenum chamber. This is normally caused by the thin, flexible sheet tending to become hemispherical either on the top or bottom or both. The hemispherical configuration given to the thin, flexible bottom sheet permits the air pallet to roll about the curved surface, possibly tilting to an extent where the load may be dislodged. The same may occur with respect to ballooning of the top sheet, except that the load may then directly roll or slide off the upward bulged surface. Ballooning of both top and bottom thin sheets accentuates both such tendencies and is particularly undesirable. As may be appreciated, proper pillowing control functions as an anti-ballooning means. Proper use of a generally rigid planar backing member of the right size will avoid the usual ballooning difficulty, but introduces additional difficulties. Where the plenum chamber is formed of thin, flexible sheet material in the general shape or configuration of a bag, such bag will tend to take a circular cross-section when fully pressurized, the true essence of a balloon, in the absence of a rigid backing member.

The prior art has provided medical patient inflatable movers or transfer apparatus and mattresses which can be easily inflated and deflated without ballooning under the patient and without the use of a rigid backing member. As noted, ballooning might result in rolling the patient to the side off the inflatable transfer apparatus. Ballooning may be prevented by either providing a stiff reinforcing structure within or along the top of the transfer apparatus or alternatively by essentially tying or securing the top sheet of the transfer apparatus to the bottom sheet in the central portion of the transfer apparatus or inflatable mattress by a series of transverse and longitudinal partition members which serve essentially to prevent ballooning without significantly restricting air flow through the structure. The partition members are preferably continuous strips of material actually partitioning off the central section of the inflatable structure from the perimeter or peripheral sections through which air under pressure injected initially at one side or end is quickly distributed about the entire outside portion of the transfer apparatus. The transverse partition members form a series of preferably rectangular chambers which in prior structures are partially closed at the ends by the longitudinal partition members which extend across the ends of the transverse partition members, preferably slightly spaced from such ends of the transverse partition members in order to provide openings for circulation of air. The transversely and longitudinally elongated partition members serve both to slightly constrict air access immediately to the central portion of the transfer apparatus to slightly delay inflation of the central portion until the outer ring or peripheral chamber partially inflates and even more importantly to physically tie the top sheet to the bottom sheet to prevent ballooning of the central portion, which ballooning might roll a patient from the center of the transfer apparatus and even off the transfer apparatus completely. The continuous or linear nature of the partition members provides a continuous line along which tacking or securing of the partition members to the top and bottom sheets can be effected to provide a more secure linear tacking line rather than a discontinuous or series of point tacking positions. However, as will be readily understood, at the end of each partition member the stress on the tacking or sewing is essentially against a single point attachment which, if such point attachment fails or parts, can continue progressively down the entire partition member disconnecting or tearing the top or bottom sheet from such partition member and possibly initiating failure of the entire transfer apparatus structure. This possibility is alleviated in the prior art by positioning the longitudinal partition members to essentially intersect or cross the ends of the transverse partition members as closely as possible. This provides a continuously tacked member at the end of each transverse partition member relieving the stress from the end of such partition members and strengthening the effective tacking at these points. This arrangement would be quite sufficient if the longitudinal partition member was closely adjacent or butted up against the end of the transverse partition member. However, since a good circulation of air must pass into the ends of the transverse chambers between the transverse partition members and, furthermore, perforating the partition members themselves with too large or capacious orifices for air passage seriously decreases the strength advantage of continuous tacking along the partition member by allowing such partition members to warp adjacent the orifices thus placing more strain upon the tacking positioned away from the orifices, it was found more effective to place the longitudinal partition member slightly away from or to space it from the end of the transverse partition members to allow easy access of air along the inside of the longitudinal partition members from the ends as well as from smaller orifices in the partition members themselves. When the longitudinal partition members were placed away from the lateral partition member, however, it allowed some slight additional tension to be applied to the end of the lateral partition members. To avoid this the longitudinal partition members of the prior art, i.e. U.S. Pat. No. 5,561,873 were deliberately made to have slightly less height than the transverse partition members so that the tension was relieved from the tacking on the end of the partition members to prevent tension failure, the additional tension being taken against the continuous tacking of the longitudinal partition members. For example, the longitudinal partition member might have a height of only five inches while the transverse partition member might have a height of six inches and the top end of the transverse partition member might even be biased slightly downwardly to more or less match the height difference between the two partition members.

While the arrangement described has proved very desirable, it has evidenced some disadvantages. One of these is that, while the transverse partition members can be secured to the top and bottom sheets at points displaced horizontally from each other in the longitudinal direction so that when the member is deflated and the top and bottom sheets collapse onto each other the transverse partition members are encouraged to lie flat or flatten out smoothly between the top and bottom sheets of the transfer apparatus incidentally providing a smoother base for a patient to lie upon, the longitudinal partition members cannot effectively lie flat in the deflated transfer apparatus. In other words, since the longitudinal partition members extend at right angles to the transverse partition members, if the transverse partition members are moved smoothly downwardly into a horizontal attitude, the longitudinal partition members are inevitably creased or folded upon themselves to accommodate the decreased clearance between the top and bottom sheets. The entire transfer apparatus, therefore, ends up with a lumpy structure between the top and bottom sheets which is uncomfortable for a patient to recline upon. In addition, the additional uneven thicknesses of fabric incidental to such creasing and folding has been found to cause non-uniform and medically confusing shadows on x-rays taken vertically through a patient lying upon one of such prior art transfer devices.

The present inventor has discovered that the problem of lumpiness under a patient and x-ray shadowing can be avoided by simply eliminating the longitudinal partition members, particularly if a perimeter wall is provided about the entire transfer apparatus rather than sewing or tacking the top and bottom sheets directly together at their outer edges, and that such arrangement can be readily combined with a heightened perimeter wall having a greater height than the transverse partition members. This provides a desirable uplift to the side of the transfer apparatus and aids in centering patients thereupon. It also adds to the feeling of security of the patient who experiences as a result no feeling of insecurity due to a perceived tendency to roll off the transfer apparatus. It also provides a more capacious internal perimeter channel about the edge of the transfer apparatus which provides a greater and quicker inflation of the sides of the transfer apparatus than otherwise, particularly if it extends entirely around the transfer apparatus from the foot section where the low pressure compressed air normally enters, in itself tending to counteract an initial tendency of the structure to balloon. In addition, the increased air flow capacity of the peripheral portion of the transfer apparatus as compared with the central section facilitates quick emergency deflation of the center portion of the transfer apparatus such as may be necessary if a patient upon such transfer apparatus suddenly requires cardiopulmonary resuscitation, or C.P.R., which is not an uncommon event, and requires a resistant surface upon which to apply compressive force to the patient's chest by hand force. It is preferable for there to also be a certain degree or amount of excess top sheet material between the ends or sides of the top sheet about the perimeter wall and the ends of the transverse partition members. This allows the top sheet to bulge up additionally around the perimeter of the transfer apparatus to provide further capacity or bulk to the perimeter raised section. There should not be too much slack, however, in order not to have the perimeter of the top sheet too much larger than the size of the transfer apparatus in order to prevent too much fitting and extra cutting in fitting and tacking the top sheet to the perimeter wall section. Preferably the ends of the transverse partition members may be turned upwardly toward the ends so that the line of tacking or sewing securing them to the top sheet is approximately directed along the natural upward curve of the raised side sections. This avoids having a single point tacking which may be easily severed by upward tension against the single point with potential progressive severing from that point along the partition member until the angle of tension becomes sufficiently close to the line of tacking or sewing to bring the actual strength of the tacking against which the tension is applied above the failure point or level. Having the effective angle of linear tacking aligned as closely as possible with the angle of tension extending along the top sheet enables the amount of tacking or sewing at the end of the transverse partition members to be less than otherwise with a significant saving in production cost.

As indicated above, one of the advantages of using longitudinal partition members as disclosed in the prior art to partially block off the ends of central chambers formed between transverse partition members in the central portion of the transfer apparatus, is to partially restrict or slow down the passage of the low-pressure air into the central rectangular chambers disposed directly under the patient, in order to slightly retard the filling of such chambers with respect to pressurizing of the peripheral portion of the apparatus to aid in counteracting any tendency of the inflatable mat to balloon under the patient. By removing the longitudinal-partition members to eliminate lumps under the patient, and x-ray shadowing when the deflated mat remains under the patient, the desirable slight initial restriction of air passage to the chambers under the patient, which discourages ballooning under the patient, is lost. However, it has been found that the same effect is obtained by providing a larger perimeter chamber, particularly along the sides of the transverse-partition members that define the central rectangular chambers, since, in this manner, the entrance of low-pressure gas to the transverse chambers is slightly, relatively restricted with respect to air passing from the larger, and, particularly higher, peripheral chamber, further decreasing any tendency of the central portion of the transfer device to balloon. The expanded peripheral sections of the transfer apparatus also provide a stiffer inflated structure particularly if such enhanced or enlarged chamber extends completely around the entire periphery of the transfer apparatus.

The combination of having an expanded peripheral chamber adjacent the ends of the transverse central chambers thus has five major advantages: (a) by raising the sides of the inflated transfer device, it provides a feeling of security to the patient as well as actual security in opposing rolling of the patient off the inflated transfer device, (b) the outer expanded peripheral chamber located, as it is, particularly at the ends of the transverse central chambers provides a slight relative restriction to air passing to the central chambers during inflation, decreasing the tendency to balloon and effectively replacing or substituting for the advantages of restricting the central transverse passages provided by longitudinal-partition members at the end of the transverse chambers when the peripheral chamber has relatively the same or lesser cross-sectional dimensions than the individual central transverse chambers, (c) the expanded peripheral chamber provides for efficient feeding of low-pressure air to all the central chambers at once, effectively encouraging more uniform inflation of the central chambers, even while slightly restricting or slowing down the feeding of air to them, (d) the enhanced size of the peripheral chamber provides enhanced rapidity of removal of air from the central chambers during deflation of the central section in emergency situations, when cardiopulmonary resuscitation or the like may be necessary for the patient and (e) the greater dimensions of the peripheral chamber provides enhanced stiffness to the entire transfer apparatus, making it easier to handle when inflated.

The inflatable transfer apparatus of the invention is designed as indicated above to be used under the patient in an uninflated condition upon a regular hospital bed already in position so that when the patient has to be moved from the bed to a gurney or stretcher for transport to a diagnostic facility such as x-ray or magnetic resonance imaging (M.R.I.) facilities or a procedure facility such as an operating room table, the transfer apparatus can be inflated and then slid off the bed directly onto the gurney or stretcher while supported by pressurized air escaping from the bottom and then at the conclusion of the patient's transport to an x-ray department or other hospital department again returned to a position adjacent the patient's bed and slid from the gurney or the like onto such bed and deflated until again required. Deflation is merely a matter of shutting off the portable pneumatic pump which supplies inflation. The inflatable transfer apparatus will then lie "dormant" upon the hospital bed until used again for transfer to a gurney or the like, meanwhile, however, providing a waterproof cover over the bed (but under the lower sheet) and being quite comfortable to the patient because the lateral partition members under the patient are smoothly folded down and there are no longitudinal partition members to bunch up or fold in half or lumps beneath the patient. If rapid emergency deflation is desired particularly in the center of the transfer apparatus under the patient an easily operated exhaust valve may be provided in the outer peripheral chamber.

In the case of many patients who are too sick to be ambulatory or transportable in a wheelchair, which is the type of patient the transfer apparatus of the invention is especially designed for, in any event, the patient is frequently also too sick to turn over in bed to relieve pressure against the skin and avoid bedsores. Nurses and orderlies thus often have the task of periodically rolling such persons partially to one side or the other. Such patients are usually a dead weight, however, and not only difficult to roll, but difficult to start to roll. The present inventor has, in order to accommodate such patients, provided on the top of the transfer apparatus of the invention two adjacent chambers designed to be inflated to form a wedge-shaped lifter, or patient roller means, designed to be used alternatively on one side of the transfer apparatus or the other. Such wedge-shaped roller sections can be separately inflated while the transfer apparatus, or the main portion of the transfer apparatus as a whole, remains uninflated. Such inflation under one side or the other of the patient will lift that side of such patient and tip the patient toward the other side, in so doing at least starting the roll of the patient toward that side and saving many a back of nurses or orderlies in attempting to initiate such rotation of the patient, which, because of the fact the average patient is very low in the hospital bed, or even sunk partway into it, can place a very significant strain on the back of anyone attempting to roll the patient. The fact that the medical personnel, either professional or nonprofessional, are usually not warmed up when attempting to turn the patient and are frequently out of shape as well, means that back injuries are by no means rare in undertaking the rolling or position changing, frequently referred to as "log rolling" of relatively helpless patients.

It is desirable in placing the patient on the partially uninflated transfer apparatus to center such patient along the mid-line of the inflatable transfer apparatus and the sew or tacking line securing the turning chambers to the center of the transfer apparatus serves this function very admirably. Even where the inflatable turning chambers are not included in transfer apparatus of the invention, however, it has been found by the inventor to be very desirable to provide a special center line down the center of the transfer apparatus to facilitate centering of the patient upon the inflated or deflated transfer apparatus. It has thus been found by the inventor to be very desirable to address the difficulty of placing the patient centered upon the transfer apparatus by providing a central indicia line. In addition, the inventor has found it to be very desirable to have the top and bottom of the transfer apparatus made from different color material to enable nursing personnel to easily distinguish the bottom of the transfer apparatus with its very many small perforations from the top without perforations and with preferably patient rolling chambers also supplied on the top. Applicant prefers to use a light color underneath and a dark color such as dark blue on the top which will not stain as easily with blood or other body fluids.

As a still further difference from the prior art, the inventor has provided an inflation sock or pair of inflatable socks at the end of the transfer apparatus which instead of having several more or less equivalent inflation orifices leading therefrom such as three even-sized openings, instead provides two unequal-sized openings, the egress opening nearest the air inlet being smaller where the pressure is greater, and the egress opening farther away near the other side of the transfer apparatus being larger to allow more air at a slightly lower pressure to exit from the sock at that point in order to attain a more even air distribution in the transfer apparatus as it is inflating.

While the provision of a larger peripheral chamber has been described as being, at least in part, attained by providing a perimeter band or wall having a greater height than the height of the central transverse partition members which are tacked to the top and bottom sheets to prevent ballooning of the central sections of the inflatable transfer device, it will be understood that the larger peripheral chamber may be attained also by lowering the height of the transverse partition members, essentially decreasing the thickness of the central portion of the inflatable transfer apparatus. This has some advantage in a relative sense, since the air volume directly under the patient is thereby decreased relatively, shortening the deflation time of the mat in emergency situations such as when the patient may require emergency cardiopulmonary resuscitation.

FIG. 1 is an isometric view of the upper side of an inflatable transfer apparatus in accordance with a generic version of the present invention in which the inflatable transfer apparatus is viewed from the upper side. Such transfer apparatus 11 is comprised of a top sheet 13 around the edges of which are attached peripheral wall members 15 which are in turn attached at their lower edges to a bottom sheet 17, shown more particularly in FIG. 2, which is an isometric view from the lower side of the transfer apparatus. Bottom sheet 17 is perforated with a number of small orifices 19 which are less than one-sixteenth to one thirty-second of an inch in diameter and usually only pin hole sized and serve when the inflatable transfer apparatus 11 is placed on a reasonably resistant surface to lift such transfer apparatus slightly above such surface and lubricate its movement over such surface upon a film of relatively low pressure air, all as known in the prior art. While the small orifices 19 in the bottom sheet 17 of the transfer apparatus 11 are shown distributed more or less evenly over the central longitudinal portion of the bottom surface of the inflatable transfer apparatus, such small orifices may in many instances only be distributed basically over the so-called "footprint" of the patient on the transfer apparatus or, in other words, basically directly under the central portion of the transfer apparatus upon which the patient actually lies. This may essentially comprise a sixteen inch wide central band of closely spaced tiny orifices with two unperforated six-inch bands on each side and two eight-inch bands of unperforated areas at the upper end and lower end of the bottom sheet 17. In general, therefore, the small orifices will occur only in the central area 17x of the bottom sheet 17 directly under the central area 13x of the top sheet 13 upon which a patient is supported and the unperforated sections of the bottom are located under raised portions 13a, 13b of the top sheet 13 on both sides and 13c and 13d at both ends described below. The peripheral wall members 15 are essentially vertical or flat all the way around in a fully inflated structure but essentially fold in half either outwardly or inwardly when the apparatus is only partially inflated or deflated.

While the small air orifices 19 are shown distributed over the entire central section of the lower sheet 17 in FIG. 2, in actual fact certain of such orifices may be blocked off where a lesser air flow may be desired to support the patient, for example, under the patient's legs. This is conveniently done by sewing blocking strips of cloth or "blockers" over the unneeded orifices, usually in the form of parallel strips of cloth. It is more convenient from a construction or manufacturing viewpoint to provide a uniform perforation pattern of the bottom sheet in a central portion by a toothed roll or the like and then block the unnecessary orifices by sewing blocking strips over such orifices, than to try to perforate the bottom sheet in certain predetermined patterns for particular transfer apparatus depending upon the weight and size of patient such apparatus is designed to support. Since the "blockers" are best attached to the lower sheet 17 on its inside surface and, in any event, do not constitute a part of the present invention, they are not shown in the accompanying drawings.

As shown in FIG. 1, the top of the transfer apparatus 11, comprising essentially the top sheet 13 is upwardly raised around the side and bottom portions 13a and 13b on each side and 13c and 13d at the upper and lower portions to provide more security for the patient who is arranged to lie centered basically along an indicia line 21 shown in FIG. 1 which may comprise preferably a sewn line along the central portion of the transfer apparatus 11 which indicia line 21 serves to indicate the central area of such transfer apparatus upon and along which a patient should be arranged. As disclosed below, such indicia line 21 may also comprise a sewing or tacking line for one side of additional expansion chambers on the surface of the transfer apparatus which expansion chambers may be used to start or initiate a roll of a patient reclining upon the surface of the transfer apparatus from one side to the other in order to readjust the position of the patient upon the transfer apparatus, usually when the transfer apparatus is in a deflated state upon a hospital bed or other surface. When the transfer apparatus is essentially free standing as shown in FIG. 2, the same raised or extended peripheral sections 17a, 17b, 17c and 17d appear on the bottom corresponding to the raised peripheral sections 13a, 13b, 13c and 13d on the top. However, when the transfer apparatus is resting on a more or less level surface as in actual use, the bottom also assumes a more or less planar configuration and the raised side portions of the top become even more pronounced. However, the same relative greater dimensions of the side portions or peripheral chambers relative to the central rectangular chambers remains the same. An inflation hose or manifold 55 is shown at the lower or foot end of the transfer apparatus leading into one side of the peripheral chamber. The end 55a of the inflation hose 55 may comprise a coupling attachable to a matching coupling, not shown, attached to a plate-like construction sewn or otherwise attached to the inside of the peripheral member wall member 15.

The peripheral wall member 15 preferably extends, as discussed elsewhere, completely about the perimeter of the transfer apparatus. However, as later described and shown, an inflation hose 55 may be arranged to be connectable to the lower end of the transfer apparatus through internal inflation socks described hereinafter, and these may be preferably contained in an extra or extended section of the inflatable mat at the bottom which section may either extend beyond the lower peripheral wall member or the peripheral wall member may be completely omitted from the lower end of the transfer apparatus. In both cases, the extreme bottom edges of the top and bottom sheets 13 and 17 may be sewn together along the bottom of the inflatable mat just beyond the internal inflation socks with which the inflation hose connects. See, for example, FIG. 26. However, the inflation hose 55 may also be attached through an orifice in the peripheral wall member 15 at the lower end of the transfer apparatus, as shown in FIGS. 1 and 2 and, in this case, the extreme edges of the top and bottom sheets may be attached directly to the top and bottom of the peripheral wall member 15 at the lower portion of the inflatable mat in the same manner as along other edges of the top and bottom sheets. If the peripheral wall member is not used at the top of the mat, the top and bottom sheets 13 and 17 will be directly sewn together at this point also. Where the inflation socks are positioned beyond the peripheral wall member, the top and bottom sheets are preferably attached or sewn to the edges of the peripheral wall member and then in addition sewn to each other beyond such wall member forming an extra chamber at the foot of the mat in which the inflation socks are contained.

The top of the transfer apparatus is preferably formed of a dark color material or sheet that will not be easily stained by blood or other body fluids, such dark color being indicated by the crosshatching 18 shown at the upper corner of the top of the transfer apparatus shown in FIG. 1. The bottom of the transfer device will be preferably formed of light colored material to contrast with the dark colored top to prevent nursing and orderly personnel from mistaking the top and bottom in the stress of moving events in a busy hospital ward. Almost any contrasting colors can be used, although it is preferred, as indicated, to use a dark color such as dark blue less likely to stain with blood or body fluids.

The central portion of the top of the transfer device as shown in FIG. 1 has certain prominent features in addition to the raised sections 13a, 13b, 13c and 13d, the most prominent additional feature being the transverse lines 14a. These define the transverse indentations defining the sew or attachment points of the transverse partition members underneath. The short longitudinal lines 14b perpendicular to the transverse lines 14a merely mark the outward demarcations of the raised contours between the sew lines or points of the transverse partition members within the apparatus as well as the lower extent of the raised sides. The diagonal lines 14c at the corners of the top of the transfer apparatus merely demark the transition between the raised sections 13a and 13b along the sides and the adjoining raised peripheral sections 13c and 13d along the top and bottom respectively of the apparatus.

The interior of the transfer apparatus 11 is shown in FIG. 3, which is a partially cut away isometric view of the transfer apparatus from the top side. FIG. 3 shows a series of transverse partition members 23 vertically oriented within the main chamber 12 of transfer apparatus 11 where such transverse partition members 23 are sewn or otherwise tacked to the bottom sheet 17 and also to the top sheet 13, although most of the top sheet 13 has been cut away in order to show such central transverse partition members 23. The fact that the transverse partition members 23 are tacked to both the bottom sheet 17 and the top sheet 13 effectively ties such top sheet 13 and bottom sheet 17 together so that the transfer apparatus 11 cannot balloon when fully inflated in its central portion where the transverse partition members 23 are located. The transverse partition members 23, in accordance with the invention, are significantly lower in height than the peripheral wall 15 so that the outer portions of the surface 13 of the transfer apparatus are raised along the edges of the top sheet 13 and in particular along the sides as shown at 13a and 13b, but also, in the generic form shown, along the upper and lower, i.e. the head and foot portions 13c and 13d. Such raised portions provide a more secure top surface arrangement to prevent a patient from rolling off the transfer apparatus or otherwise moving, possibly due to tipping of the transfer apparatus when it is being removed from a hospital bed by nursing personnel, although even a significant tipping is unlikely to actually deposit a patient on the floor, so long as no ballooning occurs in the surfaces of the transfer apparatus. Even more importantly, the slightly raised edges of the sides of the top 13 of the transfer apparatus serve to provide a more secure feeling to the patients themselves, assuming, of course, that they are aware of their surroundings, even though unable to be placed in a wheel chair or the like. An effective and desirable difference in height between the peripheral wall members 15 and the transverse partition members 23 has been found to be from about one to two inches. For example, the peripheral wall members 15 may be from approximately five inches to seven inches in height while the transverse partition members 23 may be desirably about four to six inches in height. This difference in height has been found to be very effective in providing a perimeter rim in the raised side portions 13a and 13b as well as the ends 13c and 13d and particularly on opposite sides of the transfer apparatus effective to prevent patients from having any feeling that they might roll off the transfer apparatus. While it is most important that the raised sections 13a, and 13b be on opposite sides of a patient, it will be understood that such raised portions may be extended completely around the patient not only on the top 13c but on the bottom 13d of the transfer apparatus as shown in FIG. 1.

Alternatively, however, the raised portions may only be along the sides of the transfer apparatus or may even only be along the central side portions adjacent to the main body portion of the patient. In those portions of the transfer apparatus where the raised section is not believed necessary, the height of the peripheral wall members 15 and the central transverse partition members 23 may be the same height. However, as disclosed hereinafter, the interior construction is then varied in order to provide a more or less uniform air flow chamber around the perimeter of the transfer apparatus. The top and bottom sheets 13 and 17 may then be merely tacked to the peripheral wall members on the top and bottom of such wall members in order to provide the desired configuration. The bottom of the transfer apparatus will, of course, always be basically flat over the entire bottom surface when it is placed on a reasonably level surface in order to provide good mobility of the transfer apparatus over supporting surfaces. Consequently, the transfer apparatus of the invention always has the bottom sheet exactly the size of the area enclosed by the peripheral wall members 15 and the bottoms of the transverse partition members 23 are always on the same level with the bottom of the peripheral wall members 15 when a weight is applied to the surface of the transfer device to encourage easy movement of the entire structure across the supporting surface. An exception to this arrangement may in some cases occur where the perforations 19 in the bottom sheet 17 are provided only in the central portion of the transfer apparatus 11, in the so-called footprint of the patient, as is preferred, in which case the outer peripheral portions of the bottom of the transfer apparatus may actually be arranged to be disposed at a position slightly more elevated than the bottoms of the transverse partition members so that the sides or outer portions of the bottom of the transfer apparatus, which are not supported by an air film under the transfer apparatus, may be lifted a little away from the actual surface under the transfer apparatus in order to provide slightly better or easier movement over any supporting surface. This more sophisticated arrangement has certain advantages, but in most cases is not actually necessary, since adequate adjustment for movement of the apparatus over irregularities is provided by the so-called pillowing of the bottom. It is advantageous, furthermore, for there to be at least some excess unperforated bottom around the edges of the perforated section to retard at least minimal flow of gas from the central perforated portion of the bottom to beyond the central portion.

As indicated earlier, the raised peripheral section of the top sheet not only provides a raised surface which adds to the security of the patient, but also provides an enlarged peripheral chamber which in combination with the smaller transverse chambers under the patient provides improved interchange of gas between the outer peripheral chamber and the transverse chambers between the transverse partition members 23, both in inflation, where ballooning and other non-uniformity are inhibited or counteracted, and emergency deflation where very quick deflation of the central portions of the transfer apparatus are a necessity.

FIG. 4 shows a further preferred arrangement of the transfer device of the invention, shown in less than fully inflated form, in which the central transverse partition members 23a are arranged at an angle rather than perpendicular to the top sheet and bottom sheet 13 and 17. Such angle is maintained even when the transfer apparatus is fully inflated, although to a lesser degree, and enables a deflated or deflating transfer apparatus to easily contract or decrease in height. In FIG. 4 the transfer apparatus is shown only partially inflated so the partition members 23a are essentially partially lying down or more inclined than they would be with full inflation, but because the transfer apparatus is not completely deflated, not lying flat on the bottom sheet 17. While such members would be more erect with full inflation, they never reach a perpendicular position. During deflation of the transfer apparatus the transverse partition members progressively assume a more horizontal position without any folding or doubling over of such transverse partition members. The additional length of the deflated apparatus is compensated for by the upper and lower sheets 13 and 17 adjusting horizontally with respect to each other with folding of the peripheral wall members 15 at the ends and sides of the device, where it does not matter, in order to adjust for such increased length. The advantage of the inclined transverse partition members 23a is that in the embodiment of the invention shown in FIG. 3 when the transfer apparatus is deflated and used on the bed of a patient in deflated condition, which is one of the basic uses of the invention, the transverse partition members 23 in the deflated position or condition of the apparatus can and usually will fold over on themselves in order to adjust to the decreased height of the entire transfer apparatus. In the embodiment of the invention shown in FIG. 4, on the other hand, the angled transverse partition members tend to merely lie down flat on the bottom sheet 17 rather than folding over on themselves or on each other. While adjacent partition members may actually overlap each other in the deflated condition, such overlapping is fairly smooth and does not provide the lumps or uncomfortable bumps that actual folding or doubling over of the partition members on themselves causes within the mat structure. It also does not provide false shadows on x-ray film which may arise from folding over of the partition members upon themselves under a patient lying upon the transfer apparatus and having vertical x-rays taken. The slanted arrangement of the transverse partition members shown in FIG. 4 has been provided in prior embodiments of transfer apparatus structures, but has not been combined with the raised sections 13a or 13b on the sides or 13c or 13d on the upper and lower ends of the transfer apparatus which in combination with the transverse partition members without the use of longitudinal partition members as shown in FIG. 4 provides a more desirable structure.

FIG. 5 is a partial cross section taken transversely between the partition members 23a at section 5—5 in FIG. 4 and shows one of the transfer apparatus of the invention in inflated condition showing from the side a transverse partition member 23a which is attached or tacked to the upper or top sheet 13 and to the bottom sheet 17. The upper surface of the top sheet 13 is essentially flat as will be seen across this section, although there may be some slight bulging of the top sheet 13 between transverse partition members 23a as more particularly shown in FIG. 5A which is essentially an abbreviated or partial longitudinal cross section through a transfer device such as shown in FIG. 4 at section 5A—5A in FIG. 4, but in which the transfer device of the invention is essentially fully inflated as in FIG. 5 and the top sheet 13, not shown in FIG. 4 at the cross section, and has been filed in. In FIG. 5, on the other hand, the section line passes through the transfer mat shown in FIG. 4 essentially exactly at the point at which the top of a transverse partition member intersects with the upper or top sheet 13 so that the two essentially coincide and the top of the transverse partition member 23 appears also to be the top sheet 13. The raised sides of the transfer apparatus or mat 11 comprising the upwardly curved portion of the outer raised portions 13a and 13b of the top sheet 13 are clearly shown in FIG. 5 and provide the tops of open peripheral chambers.

FIG. 5B is an abbreviated cross section similar to the cross sectional view of the transfer apparatus or mat of the invention shown in FIG. 5, but including a preferred arrangement of the transverse partition members 23ab in which the outer end 25 of the partition member 23ab is upwardly curved with a configuration such that the curvature of the upper surface of the section 13b of the top sheet 13 is a direct line continuation of the angle of the top sheet 13 as it is tacked to the top of the transverse partition member 23ab. This relationship is obtained by having the end 25 of the transverse partition member 23ab turned upwardly so that it is a direct continuation of the upward curvature of the upwardly extended portion 13b of the top sheet 13. This provides tension upon the tacking along a line of tacking rather than tension directed against a single tacking point and makes a much more secure tacking arrangement. As will be seen, FIG. 5B shows only one-half of a transfer mat and cross section, but it will be understood that the other half will be exactly the same, only reversed with respect to what is shown in FIG. 5B.

FIG. 6 is a longitudinal cross section of an embodiment of a transfer apparatus or mat of the invention similar to that shown in FIG. 4 and shows such transfer mat in fully inflated condition with the raised section 13a extending upwardly along the side of such transfer mat. It will be seen that the section of the transfer apparatus in which the raised section 13a occurs does not in FIG. 6 run the length of the transfer mat, although, as indicated above, it could and, in fact, in FIG. 8 discussed below a similar arrangement is shown where the raised section 13a extends along the entire longitudinal extent of the transfer apparatus. FIG. 6 also illustrates an arrangement in which the head and body portion or upper portion of the inflatable transfer mat is higher than the lower portion which supports the legs of the patient. This is desirable in many cases in order to keep the top sheet 13 from bottoming out on the lower sheet 17 with a heavy patient. Such bottoming out will occur only usually over the extent of the body of the patient and particularly at the hips and possibly the shoulder section, but almost never over the leg portions unless the patient's weight is somewhat grossly maladjusted or maldistributed.

FIG. 7 is a longitudinal cross section similar to the cross section shown in FIG. 6 which, as indicated there, is a longitudinal cross section along a transfer apparatus similar to that shown in FIG. 6. In FIG. 7, however, it will be seen that the transverse partition member arrangement is similar to that shown in FIG. 3 in which the transverse partition members 23 are vertically oriented during full inflation rather than being maintained or held at an angle. FIG. 7 is a cross section, therefore, essentially along a longitudinal section line in FIG. 3 except that the upwardly extended peripheral side chamber 13a only extends part way along the side of the transfer apparatus as in FIG. 6.

FIG. 8 is, as indicated above with respect to FIGS. 6 and 7, a full longitudinal cross section of a transfer device similar to that shown in FIG. 4, at section 8—8 in which the raised section 13a extends completely along the edge of the transfer apparatus and the partition members 23a in the lower portion of the device or mat of the invention are lower than the same numbered sections under the remainder of the body as also shown in FIG. 4.

Figure 9:
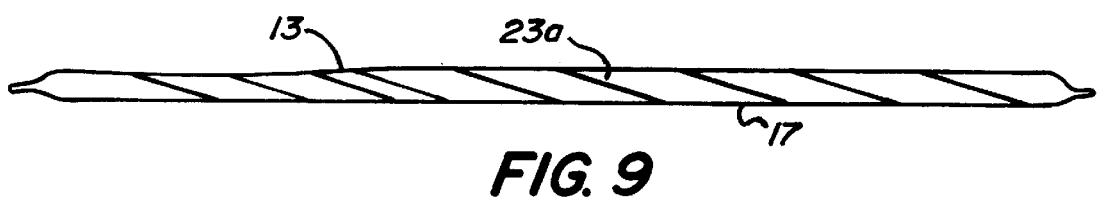
FIG. 9 is a longitudinal section through a deflated or partially deflated embodiment of the invention.

FIG. 9 shows one of the transfer mats of the invention in longitudinal section in a condition in which the transfer mat has been almost completely deflated such that the slanted transverse partition members 23a shown in FIGS. 4, 6 and 8 are laying down more or less smoothly to the point where the transfer mat is substantially completely deflated and such transverse partition members 23a may overlap slightly with each other, but will not fold in half, therefore, providing a much more comfortable deflated mat for a patient to lie on while supported by an underlying bed.

In a preferred embodiment of the invention, the transverse partition members are so dimensioned and spaced that they do not overlap with one another, but lie down flat upon the bottom of the mat, i.e. upon perforated sheet 17, without overlapping. For example, transverse partition members having a height or vertical dimension of 5 inches may be attached to sheets 13 and 17 spaced six inches on each of the top and bottom from the next adjacent transverse partition members allowing a six inch clearance for the length of said transverse members to be laid down. Even more preferably, the space between the partition members will be dimensioned to be almost exactly the same width, with an additional very small clearance, as the vertical dimensions of the transverse partition members. This effectively eliminates varying thicknesses of cloth along the bottom, makes the mat very comfortable to lie upon and eliminates x-ray shadows except for very thin straight lines which are obvious artifacts and therefore easily disregarded.

Figure 10:
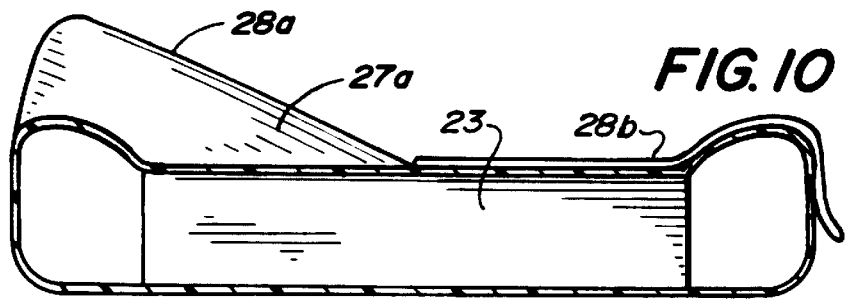
FIG. 10 is a transverse section through an improved embodiment of the invention shown in an inflated condition.
Figure 11:
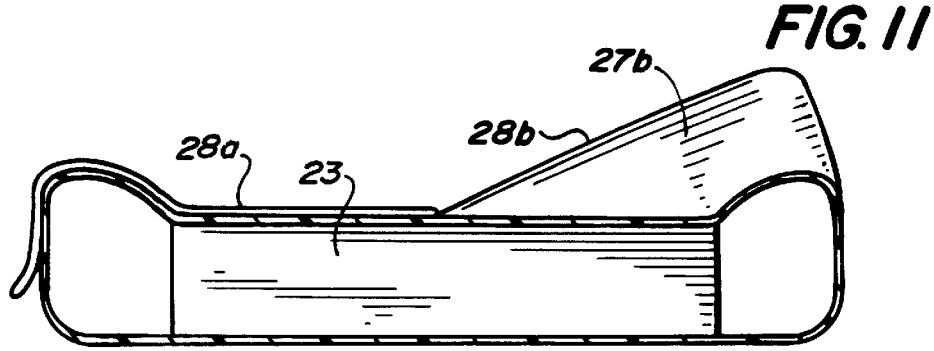
FIG. 11 is a transverse section similar to FIG. 10 showing inflation of the opposite side.
Figure 12:
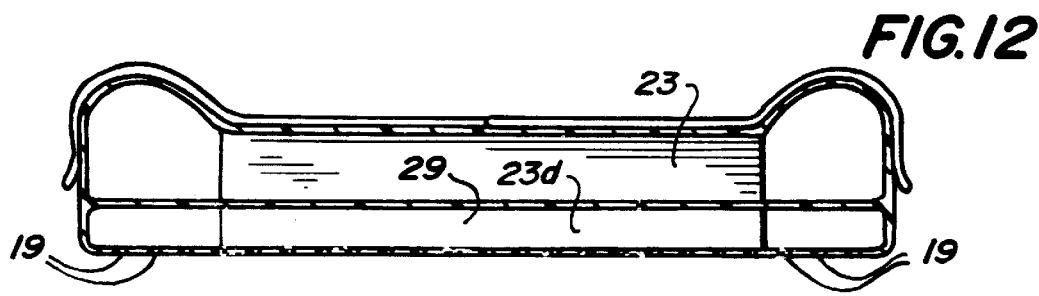
FIG. 12 is a transverse section through a further embodiment of the invention.
Figure 13:
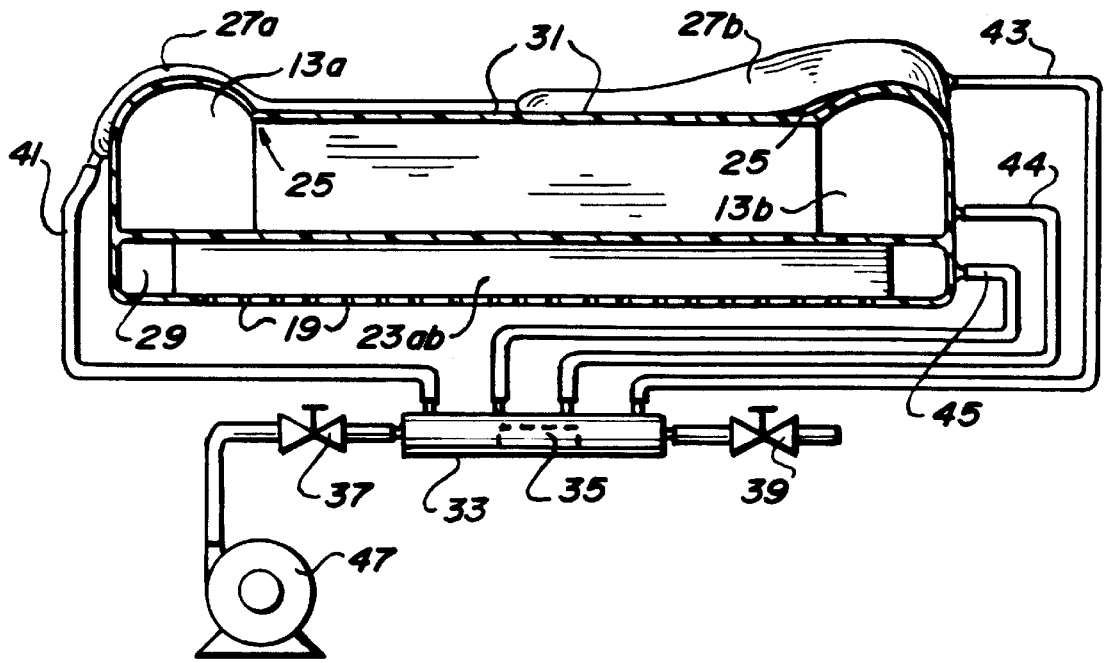
FIG. 13 is a diagrammatic representation of a valving arrangement for the embodiment shown in FIG. 12.

As indicated above, an important part of Applicant's invention in a preferred embodiment is the provision of an additional chamber on top of the transfer mat or apparatus of the invention on each side of such transfer apparatus in a position such that when the additional chamber is inflated on either side it tends to roll the patient to the other side making it much easier for nursing personnel attending to the patient to continue the roll to whatever position they desire. Thus, while the additional chambers when inflated do not completely roll the patient to the side, they do have the ability to initiate a roll and continue it at the most difficult portion of such roll so that such roll can be continued more easily by nursing personnel to any position which they desire. While the expandable or inflatable roll chambers will normally be used while the entire transfer apparatus is deflated and supported on a hospital bed ready to be inflated for transporting or transferring the patient to some other place, for example to an x-ray facility or the like, in those cases where the transfer apparatus may be used for a significant period as a primary support for the patient, for example, in an emergency room or waiting in other departments pending the completion of certain tests or the like, it may be desirable at times to use the roll chamber or roll starting chamber to change the position of the patient on an inflated transfer apparatus. In view of this and to better show the relationship of the rolling chamber to the entire apparatus, there is shown in FIGS. 10 and 11 a transfer apparatus in inflated cross sectional view such as shown, for example, in FIG. 5, but having an additional pair of chambers 27 on top designated either 27a or 27b, the chamber 27a being to the left and the chamber 27b being to the right in the figure. In FIG. 10 chamber 27a is shown inflated in the condition in which it would serve to start a rotation of a patient lying on the transfer apparatus and chamber 27b is shown deflated in the condition in which it would normally be. In FIG. 11 the opposite condition is shown in which the chamber 27b is inflated and the chamber 27a is deflated. In FIG. 12, on the other hand, both chambers 27a and 27b are shown in deflated condition. FIG. 12 also shows a structure in which there is a further bottom chamber 29 in the transfer apparatus from which the small air film developing orifices 19 actually lead. This more sophisticated arrangement at times provides both a more comfortable and a more expeditiously moved transfer apparatus. Furthermore, in most cases where it may be desired to permanently inflate the main portion of the transfer mat or apparatus and leave such main body portion inflated to support a patient for long periods, for example, in situations in which, due to some catastrophe or other, all the beds in a hospital may be filled and it may be necessary to use stretchers or the like in the halls or places not normally used for housing patients, the portable transfer apparatus may be pressed into service as a permanent support or bed for a patient. Normally this will not be done unless the chamber 29 is separate from the main body portion 12 of the transfer apparatus. Otherwise the portable pump of the transfer apparatus would have to operate continuously in order to keep the transfer mat or apparatus completely filled with air and prevent it from collapsing. In a case where the transfer apparatus may be used to provide temporary hospital bed space, a different valve arrangement must also be provided in order to provide air separately to both the main portion of the transfer apparatus and the lower supporting chamber. This is quite practical, however, particularly in an arrangement including the roll chambers 27, since such chambers would normally be used with the transfer apparatus itself in deflated condition and therefore must be separately inflatable and, in any event, the two chambers 27a and 27b will always be inflated separately, requiring, therefore, separate valving to individually inflate such chambers. Consequently, since separate valving must be used in any event, it is relatively simple or easy to add the further valving to separately inflate the chamber 29, or "plenum chamber", from the main portion or chamber 12 of the transfer apparatus and to block exit of the air from the main portion or chamber so that the transfer mat or apparatus may be used as a permanent support for patients or, in other words, as an emergency bed. A suitable valve for such use is shown in FIG. 13 in which it may be seen that a multiposition valve may be used in the embodiment shown. It will be noted in FIG. 12 that there are separate transverse partition members 23 and 23d in both the main chamber 12 and the plenum chamber 29.

FIG. 13 is a diagrammatic cross sectional view of a combined preferred embodiment in accordance with the present invention, in which there is (a) a separate lower support section 29 in which a plurality of orifices 19 provide an underlying air film on which the transfer apparatus may be moved, (b) raised side sections 13a and 13b which provide additional security for a patient lying on the central portion 31 of the transfer apparatus 11, (c) upcurved ends 25 at the upper ends of the transverse partition members 23, which upcurved ends 25 have the same essential angle as the angle at the beginning of the ends of raised portions 13a and 13b, (d) two separate upper chambers 27, designated 27a and 27b, which serve as the rolling chambers on top of the main body of the transfer apparatus and (e) a multiple way valve 33 having an internal valve distributor 35 shown diagrammatically in broken lines which can be moved to any of four different positions to connect either an air inlet 37 or an air outlet 39 with included valves connected to the central distribution valve 33. Distribution hoses or conduits 41 to the patient roll chamber 27a, 43 to the patient roll chamber 27b, 44 to the main body 12 of the transfer device or 45 to the separate support or plenum chamber 29 on the bottom of the transfer apparatus 11, are provided. If the valve 37 is open, air from a portable pneumatic supply pump 47 operated by both or either of battery power or central electrical distribution derived power will be directed to any of the lines to which the central distribution valve 33 is turned. Meanwhile, exhaust valve 39 will be closed so that air pressure is held in any of the chambers having no other outlet except in the lower support chamber 29 where air normally escapes through orifices 19 providing an air film for transport over a reasonably planar surface. On the other hand, if valve 37 is closed and valve 39 is open, air will be exhausted through the central distribution valve 33 and exhaust valve 39 to the open atmosphere from any chamber or hose system to which the valve 33 is turned. The manual valve system shown is simple and effective, even though requiring multiple manual operation or attention. However, there are more sophisticated valve systems either available on the market or capable of being designed by one skilled in the valve art to carry out the same operations in less time and with fewer manipulations, and the particular type or construction of the valve or valve system constitutes no part of the present invention except broadly for the use of a multiposition valve to provide proper access to any of the chambers. Electrically operated automatic valves, including push button selection of valving positions, may be used.

Figure 14:
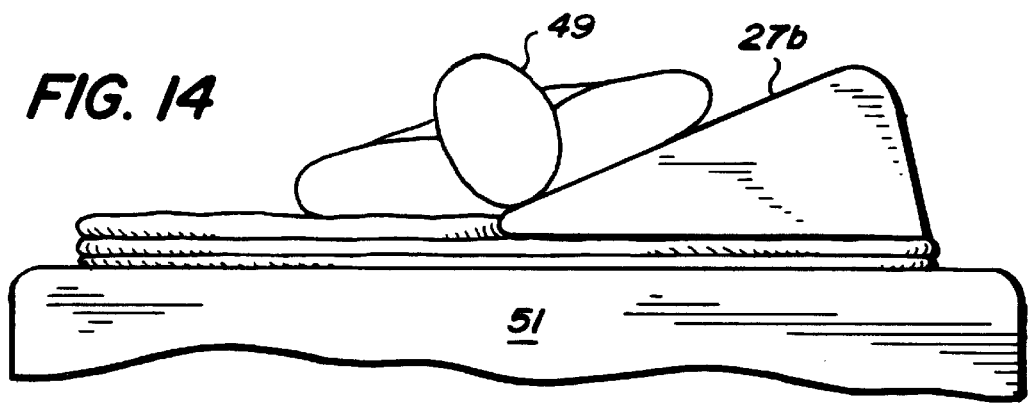
FIG. 14 is an end view of use of the embodiment of the invention shown in FIGS. 12 and 13.
Figure 15:
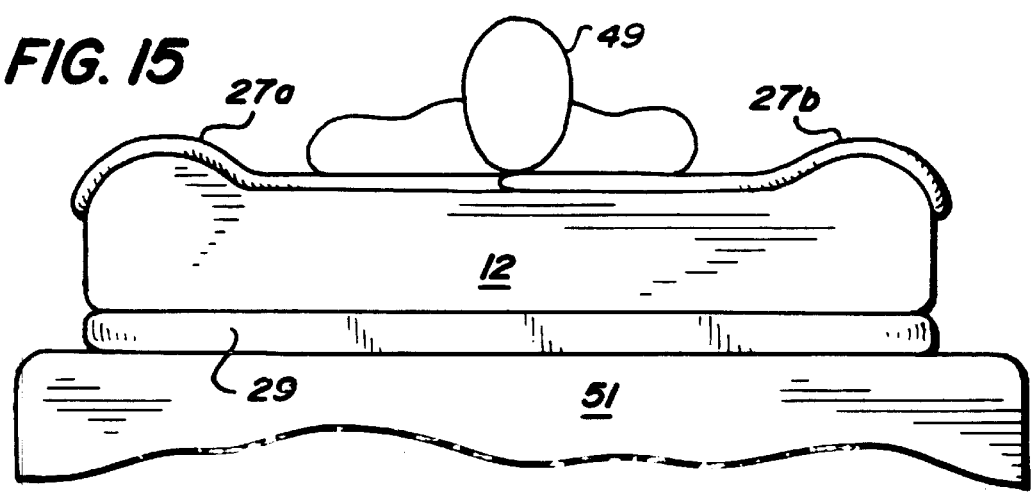
FIG. 15 is an end view of the use of the embodiment of the invention shown in FIGS. 12 and 13.

FIG. 14 is an end view of the embodiment of the invention including the so-called "log rolling" chambers 27 shown in FIGS. 10, 11, 12 and 13 in use on a hospital bed or other bed such as a bed in a nursing home or the like, in which the main portion or body of the transfer apparatus 11 is deflated along with the roll chamber 27a while the roll chamber 27b is inflated to roll a patient 49 on the bed 51 slightly to the left which is sufficient to get the patient started in the so-called log roll maneuver. If it was desired to transfer the patient to some other location, the main body 12 of the transfer apparatus would be inflated and the roll chamber 27b deflated as shown in FIG. 15, whereupon the transfer apparatus 11 can be pushed or slid off the bed onto a gurney or the like and the patient transported upon the gurney still lying upon the transfer mat to the location desired. For illustrative purposes, a bottom support chamber 29 is not shown with the transfer device 11 in FIG. 14, but is shown associated with the transfer device 11 shown in FIG. 15.

FIG. 16 is a diagrammatic view of one end of a transfer device in accordance with the invention showing the use of an improved air inlet to the main body 12 of the transfer device. Previously used air inlets have been essentially as shown in FIG. 17, which is also a partially broken away end of a main body 12 of a transfer device, in which an internal "sock" or tube 53 is sewn or otherwise attached to the inside of the main body portion 12 of the transfer apparatus. There are two socks 53a and 53b sewn into opposite sides of the transfer apparatus adjacent to each other. Only the initial inlet portion of the sock 53b can be seen in either of the FIGS. 16 or 17 as the remainder of such sock is obscured by the body of the adjacent sock 53a. An air supply hose 55 having a conical fitting 57 on the end jam fits into an opening in the perimeter wall 15 at one side or the other of the end of the body portion 12 of the mat. Such fitting is usually held in the opening in the perimeter wall 15 by a Velcro (R)-type latch or strap, not shown, that snaps over the outer end of the fitting 57. Preferably there is a snap fastening on the inside of the strap which interconnects with a matching snap on the nozzle of the hose. The "socks" or tubes 53a and 53b have conventionally been provided with three or more orifices 59 of similar dimensions more or less equally spaced across the length of the sock or tube 53 to distribute air evenly across the end of the body portion 12 of the transfer apparatus particularly so that the transfer apparatus will not inflate unevenly and possibly dump a patient off one side. However, the present inventor has now found that superior results may be had, so far as even inflation is concerned, if the sock 53 is, as shown in FIG. 16, provided with essentially only two orifices 61 and 63, orifice 61 being near the inlet orifice in perimeter wall 15 into which the fitting 57 of hose 55 fits, and orifice 63, which is at least one third larger but less than one half larger in size than orifice 61, is provided at the far end of the sock 53, but facing inwardly toward the main body 12 of the transfer apparatus. This arrangement of orifices places the larger orifice farther from the air inlet and serves to much better distribute pressurized air evenly within the body portion 12 of the transfer apparatus 11.

The present applicant has found that his improvements to the conventional transfer apparatus have provided a very much more satisfactory transfer apparatus that can be used for multiple purposes. The elimination of the more conventional longitudinal partition members provides a more comfortable transfer apparatus for patients and eliminates otherwise troublesome x-ray shadows, and the combination of only the transverse partition members with raised upper side surfaces on the transfer apparatus provides a more secure surface for the patient to lie upon. Moreover, it has been found that the additional volume of the peripheral chamber in the transfer apparatus as a result of the additional height or raised sides improves the inflation characteristics as the outer edges or outer peripheral chamber of the transfer apparatus tend to fill preferentially to the more central portion in the area of the transverse partition members further decreasing any likelihood of ballooning or unequal initial inflation that may or could tend to roll the patient toward the edge of the transfer apparatus during inflation. This, in combination with the advantages of having roll or "log rolling" chambers on top of the transfer apparatus, provides a more versatile transfer apparatus for hospital use. Since the use of separate log rolling chambers requires the use of suitable valving for differential inflation of various parts of the transfer apparatus, it is also now more practical and economical to provide a separate bottom support section from which an air film is supplied to make the transfer apparatus easily movable from one support surface to another and thereby rendering the transfer apparatus practically usable in a hospital environment not only as a transfer apparatus but for separate emergency use as a hospital bed or cot during catastrophes and the like. The entire combined transfer apparatus thus becomes much more adaptable to various conditions whereas such specialized apparatus has, as a practical matter, been necessary in the past. The further inclusion of a differential color for the bottom and the top of the transfer device as illustrated in FIGS. 1 and 2, where in FIG. 1 the hatching 18 indicates a blue color, and the use of a central sew line 21 as illustrated in FIG. 1 to aid in centering the patient both to keep such patient over the transverse partition members which serve as anti-ballooning restraints and to arrange the patients for best operation of a "log rolling" option where this is provided, is very desirable as it facilitates quick and efficient use of the apparatus by hospital personnel who are frequently in a rush due to the press of events in active hospital wards or the like and can otherwise, it has been found, easily make mistakes in positioning both the transfer apparatus as to the correct side for patient use and correct arrangement or orientation of the patient upon the apparatus.

One very important improvement in the present invention is the provision of the expanded peripheral chambers 13a, 13b on the sides and, in certain preferred constructions, 13c and 13d at the upper and lower ends of the transfer apparatus. These expanded peripheral chambers not only provide raised outer sections on the top of the transfer apparatus or mat, but also enlarged internal capacity or air flow chambers completely around the outside of the apparatus allowing a quick interchange of gases from the air supply to such chamber and then to the central transverse chambers underlying the patient. The same passageways also enable gases to quickly exhaust from the central portion of the transfer mat or device 11 to the expanded outer reservoirs in the event it is necessary to instantaneously deflate the transfer device and particularly the central portion of such transfer device underlying the patient in an emergency such as, for example, a cardiopulmonary emergency. A single emergency deflation valve 16 can be placed anywhere on the outer periphery of the expanded outer chamber, see for example the rear top surface of the transfer apparatus in FIG. 3, or in the outer peripheral band 15, see the lower left corner of the transfer FIG. 3, and, by releasing the pressure in such outer peripheral chamber by opening such emergency valve, pressure is immediately released from the outer expanded peripheral chamber area allowing air to quickly exhaust from the central portion 13x of the apparatus under the patient allowing such patient to be immediately deposited upon any firm surface underlying the transfer apparatus to facilitate cardiopulmonary resuscitation or the like. The large or expanded peripheral chamber considerably facilitates the quick exhaustion of all air from the central portion 13x of the apparatus with the use of only a single valve in such outer periphery or by merely turning off the pump, which also leads into the outer peripheral chamber, through the effect of the weight of the patient upon such middle or central portion 13x of the apparatus. The weight of the patient quickly exhausts the air in the central portion of the apparatus from the orifices under the patient, aided, if the central chamber is thinner than usual, but the concomitant decrease in volume, while the side or peripheral chambers are available to store excess air until it has time to slowly exhaust through the central orifices even as medical personnel work on the patient. Of course, if the preferred additional emergency exhaust valve is used, the peripheral chamber quickly exhausts air from the central chamber so that almost instantaneous deflation of the central portion of the apparatus is attained sufficient to work on a patient supported thereon.

While, as indicated above, it is preferred to have a transfer apparatus which has an elevated chamber all around the periphery of the inflatable mat, providing both an upward inclination or raised section at the sides of the top sheet to provide an enhanced feeling of security to the patient or user, but also a larger or enhanced peripheral air space for better distribution of air both during inflation and deflation, other forms of the inflatable mat may be constructed. For example, since the weight of a patient is concentrated in the torso from and including the hips to the shoulders and also in the head, it is sometimes desirable to provide wider and higher central transverse chambers in the upper portion of the transfer apparatus under the portion of the upper sheet that supports the upper portion of the body of a patient and relatively thinner and lower height chambers in the lower portions of the transfer apparatus. The relative sizes of the transverse chambers (which as explained above, are really only divisions in the central chamber of the mat formed by the transverse partition members) may thus be varied. Basically, it is desirable to have thicker pad or mat sections under the principal portions of the body so that the body of the patient can sink into the heavier sections farther without touching or bottoming out on the lower or bottom sheet. If bottoming out occurs the patient would not be resiliently supported and the exit orifices or air orifices in the bottom sheet might be occluded preventing proper mobility of the transfer apparatus. Also, on a uniform thickness mat the upper portions of the body sinking farther into top will tend to leave the legs relatively elevated, which can be uncomfortable for the patient and even give a patient the feeling their blood is rushing to their head. Preferably, therefore, the lower central section of the inflatable mat will be lower than the upper central section. Since these inflatable mats are operated on relatively low pressure air, more sinking into the mat will be experienced than with a firmer bed such as a hospital bed and it is desirable, therefore, to make allowances or adjustments to maintain the patient as much as possible in the same position as they would assume in an ordinary bed.

In addition, since the lower portion of the inflatable mat not only supports relatively lighter portions of the body, but also is normally the area in which the inflation air may be injected into the mat, the lower portion may take a different configuration to accommodate these factors as well.

While FIGS. 10 through 12 and 13 through 15 show various cross sectional views of embodiments of the invention having extra so called "log rolling" chambers 27a and 27b on the top of the transfer apparatus of the invention, and each shows the chambers 27a and 27b as being basically triangular in form, a configuration such chambers tend to take in the event a patient is reclining on the inside of the top of the upper surface of such chambers, it should be understood that the chambers 27a and 27b actually, unless the chambers are restricted in some way as to shape, tend to balloon or assume an upwardly humped or curved configuration rather than a right triangular configuration as shown. In order to achieve a basically triangular configuration as shown, it is necessary for such configuration to be maintained either by some outside shaping pressure such as a patient lying on one side or else to have inside restrictions to maintain the general shape of the patient rolling chamber. While a rounded, i.e. ballooned inflated upper surface of the chambers may effectively aid in log rolling a patient from side to side, it is generally most beneficial for such chambers to have an evenly sloped outside which may preferably take a general triangularly shaped outer configuration. Since the inflated angle predetermines the maximum amount of inclination and the resulting wedging force which may be applied against a patient to aid in rotating or turning such patient, the allowed surface angle of the rolling chamber assumes some importance. Such angle should broadly be about 45 degrees inclination from either horizontal or vertical plus or minus approximately 10 degrees or more preferably plus or minus 5 degrees. It has been determined that the most effective way to maintain the desired configuration of the rolling chambers, including the angle of the top, is to provide internal ribs or reinforcements to hold the chambers in shape. Thus, in FIG. 18, which is a top isometric view of a transfer apparatus in accordance with the invention, the outside covering or the outside sheet of the patient rolling chambers is shown partly or mostly removed revealing a series of triangular ribs 61 which are normally attached on both sides to the two slopes of the rolling chamber. The ribs are sewn or heat molded or otherwise attached or connected within the chambers 27a and 27b to the outer sheet or casing 28a or 28b on their upper side and to the top sheet 13 of the inflatable transfer pad itself on their under side. It should be noted that the ribs 61a are raised into their patient "log rolling" configuration on one side of the transfer apparatus and the ribs 61b on the other side are in a retracted position or laid down upon the top of the apparatus. In actual use only one set of such ribs will be raised at a time and the other set will be laid down or flattened out upon the surface of the transfer apparatus in their recessed or unused position as shown for ribs 61b. The ribs 61a are shown in a perpendicular position, but could also in their fully erected position be in a slightly inclined attitude to facilitate laying such ribs down smoothly somewhat in the same manner as the transverse partition members 23a seen in FIG. 4 and are then partially inclined when fully erected in the direction in which they are to lie when the mat is deflated. Thus when the inflation of the slanted patient rolling chambers 27a or 27b is accomplished to initiate the beginning of a roll or to partly roll a patient on the surface of the transfer apparatus, the rolling chamber in which one of the sets of ribs 61a et al. or 61b et al. are located is partially or fully inflated causing the outside triangular surface of the patient roller chamber to be raised by inflation and incidentally raising the ribs 61a et al. or 61b et al. into normal operating or support position. The ribs are, as indicated above, sewn, heat tacked or welded inside of the rolling or rotation surfaces 28a or 28b to maintain the outer surface of said rolling sheets in the desired triangular shape. Otherwise the surface would tend to balloon to an indeterminate shape.

FIGS. 19, 20, 21 and 22 respectively show a diagrammatic plan view, a diagrammatic bottom view, a longitudinal section and a transverse section through one successful commercial type design of the inflatable transfer mat of the invention. In FIG. 19 there is seen a plan view of the top of an inflatable mat in accordance with the invention which mat incorporates the preferred arrangement of transverse partition members, not shown, but wherein the attachment points or sew lines 71 of which partition members are visible on the top surface. Such sew lines 71 thus indicate where the top of each transverse partition member 23a, see FIG. 21, is attached to the top sheet of the inflatable mat. The bottom view shown in FIG. 20 also shows the sew lines 73 which mark the attachment points of the transverse partition members 23a to the lower sheet 17 of the transfer mat. It may be seen that these sew lines are displaced upwardly toward the upper portion or top of the bottom sheet with respect to the same sew lines on the top sheet. This displacement represents the inherent inclination of the transverse partition members 23a which causes them to fold smoothly downwardly when the transfer apparatus is deflated. It will also be noted that the sew lines on the lower portion of the upper sheet have curved ends 71a, this representing the relatively more depressed central leg section of the transfer mat provided as indicated above to keep the legs of the patient from being elevated over the head and body portions of the patient. The ends of the transverse partition members extend partway up the side of the raised sides of the transfer mat and since the partition members are attached to the top sheet of the transfer mat in a preinclined or inclined or angled disposition, the portion that extends up the side of the raised sides inherently appears curved when viewed along the sew line. The center sew line shown at 75 in FIG. 19 which does not actually attach anything to the top sheet unless the roll chambers 27a and 27b shown in some previous views are used, provides a useful indicia line for arranging a patient along the center portion of the inflatable mat over the air perforations on the bottom.

FIG. 21 is a longitudinal section through the transfer apparatus shown in FIGS. 19 and 20 showing the transverse partition members 23a including a preferred differential height between the various transverse partition members and relative differences in spacing. Each chamber between partitions is assigned a position or chamber number from 1 through 10, the lowest number designations being at the head end and the highest number designations being at the foot end. It will be either noted or understood that chambers 1 through 6, which are essentially head and body support chambers, are somewhat wider than body support chambers 3 through 6 and that leg support chambers 7 through 9 are relatively narrow and of less height (the section being taken in the center along the longitudinal axis) and that foot chamber 10 is again wider and higher to support the additional weight of the feet. A higher chamber, of course, provides more clearance between the top and the bottom sheets to prevent bottoming out. However, a wider chamber also allows more relative expansion of the top sheet upwardly, also providing more cushioning.

In FIG. 21 it may also be seen that the lower end of the mat contains the air injection socks. While not shown, the lower end of the mat may come to a more or less pointed configuration which provides room essentially for the air inlet socks shown in FIG. 16 or FIG. 17 which are relatively narrow and do not require the height of a perimeter band. The top and bottom sheets 13 and 17, in such case, therefore, can be sewed or otherwise attached together at the bottom along the air inlet section to simplify the construction. See in this regard FIG. 26 described below.

FIG. 22 is a partial transverse section through the transfer apparatus of the invention along transverse section 22–22 of FIGS. 19 and 20 and shows a transverse partition member 23a the expansion of the top of expanded chamber 13a behind, plus the expanded peripheral chambers 13a on one side.

The arrangement shown in FIGS. 19 through 22 has been found to be a very satisfactory overall arrangement and constitutes one form of applicants best commercial embodiment of the invention at the present time. However, as indicated above, other arrangements can also be effectively used.

While it is preferred, as explained, to have a continuous enlarged peripheral chamber to effect more uniform inflation and quick emergency deflation as explained, the same effect can be obtained to a somewhat lesser extent by having larger chambers of the same height as the center sections, but wider dimensions at those portions of the transfer apparatus as shown in FIGS. 6, 7 and 8, for example, wherein the top and bottom open sections are wider than the central transverse chambers between the transverse partition members 23. The extended width of the bottom and top chambers 16 and 18 shown in FIGS. 6, 7 and 8 should be overall the same or preferably greater in volumetric value than the value of the side chambers 13a and 13b shown, for example, in FIG. 5, to compensate for the change in dimensions at the transition between the two.

Figure 23:
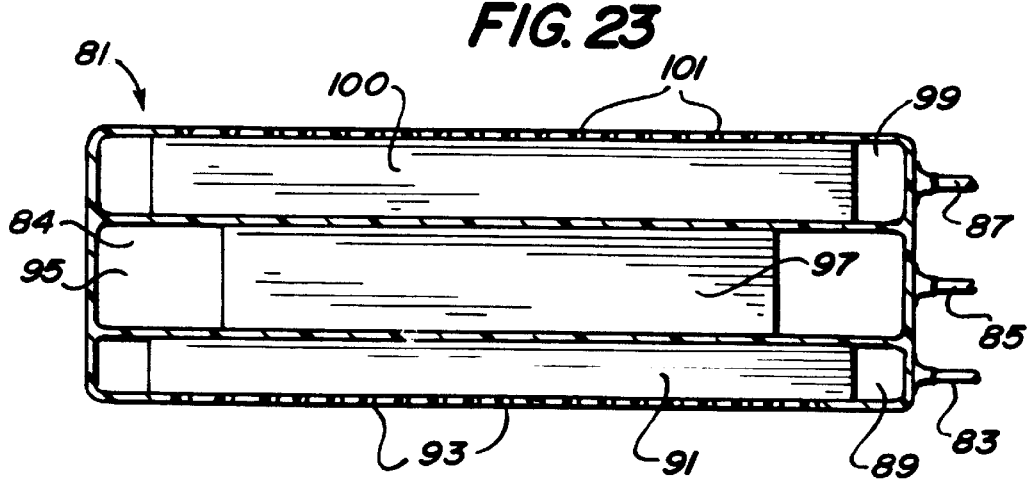
FIG. 23 is a transverse section through a transfer device incorporating a low air loss chamber on top.

FIG. 23 shows a further embodiment 81 of the invention in which a transfer apparatus is equipped with three separate chambers 82, 84 and 86, chamber 84 being the main or central support chamber, chamber 82 being a low air loss chamber on top and chamber 86 being a plenum or support chamber on the bottom. The peripheral portion of the main chamber 84 designated here as 95, is not elevated because it is essentially covered by the upper low air loss chamber 82 designed to blow low pressure air past a patient's body to prevent over moistness of the skin, and thereby prevent the breakdown of the dermal layer with resulting bedsores and various other infections. However the peripheral chamber 95 is made particularly commodious or large beyond the edge of the transverse partition number 97 to obtain some of the benefits of a raised or expanded peripheral chamber. The particular embodiment of the transfer apparatus of the invention, instead of being equipped with top-mounted so-called log rolling chambers, as described above is, instead equipped with the low air loss chamber 100 having small perforations 101 in the top through which air at low pressure is blown upon and across the body of the patient. The transfer apparatus is also equipped with a separate plenum chamber 86 under the main chamber 84 equipped with air orifices 93 and transverse partition members 91 (only one of which is visible) extending across the chamber to prevent ballooning. A similar set of transverse partition members 100 extend across the upper low air loss chamber 82 to prevent ballooning of this chamber. Since only a small amount of air is necessary for the low air loss chamber which is equipped with very small orifices 101, hence its name, and it is desirable for the air which passes from such orifices to pass freely away from the patient's body as well as away from the underlying apparatus, the upper chamber 82 is not equipped with raised peripheral or expanded peripheral chambers. However, as explained above, the central chamber 84 is provided with a particularly commodious peripheral chamber to allow quick passage of air around the periphery of the entire chamber and into and out of the transverse chambers between the transverse partition members 97. Each of the chambers 82, 84 and 86 is provided with its own anti-ballooning transverse partition members 100, 97 and 91 as well as its own air inlet 87, 85, 83. As will be recognized, any of the chambers can be deflated simply by cutting off the air supply derived from a suitable valve arrangement guide as shown, for example, diagrammatically in FIG. 13. The embodiment of FIG. 23 discloses an inflatable transfer apparatus in which there is provided capability not only for air lubricated transfer of a patient from a bed to a gurney or vice versa, but has the capability to provide low air loss air to prevent over moisturization of a patient's skin during prolonged confinement to bed, and also has the ability to be used as an emergency bed during emergency conditions.

Figure 24:
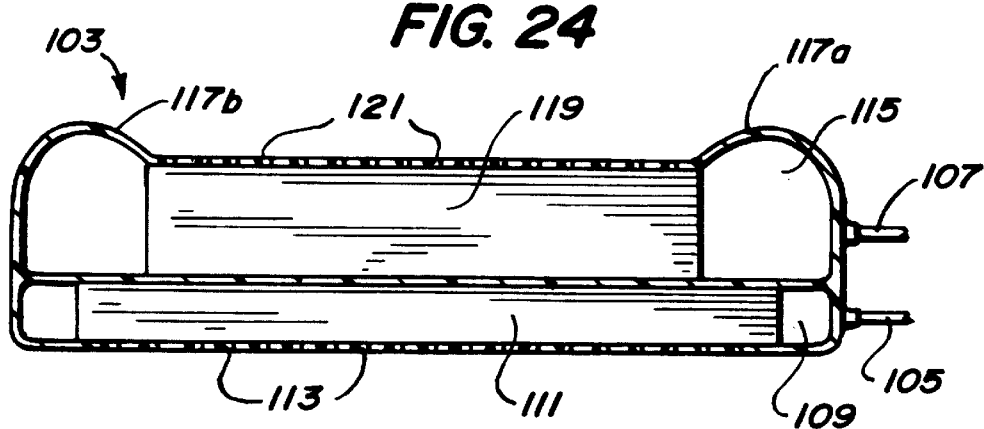
FIG. 24 is a transverse section through a transfer device in accordance with the present invention incorporating a low air loss modification.

FIG. 24 shows a transverse section of an alternative embodiment 103 of the transfer apparatus of the invention having two chambers 104 and 106, the top chamber 104 having a raised peripheral chamber 115 surrounding the central section containing transverse partition members 119 as described for earlier described embodiments, and the second lower chamber 106 constituting a second plenum chamber from which lower pressure air escapes to lubricate movement of the transfer apparatus from one support structure to another such as from a bed to a gurney or vice versa. The upper chamber is equipped with integral small low air loss orifices that provide a low pressure flow of air about the body of a patient as a soothing stream that drys the skin of the patient and prevents breakdown of such skin resulting ultimately in bed sores and other like infections. In this embodiment of the invention, there are only two separate air feed hoses to the two separate chambers 104 and 106 so the bottom plenum chamber can be used when it is desired to move a patient from one hospital facility to another, i.e. especially from a bed to a gurney for transport to an x-ray, MRI or other facility or vice versa, and the top chamber which can be used as a permanent low air loss cover for a bed or in an emergency as a temporary bed itself providing low air loss treatment capability.

Figure 25:
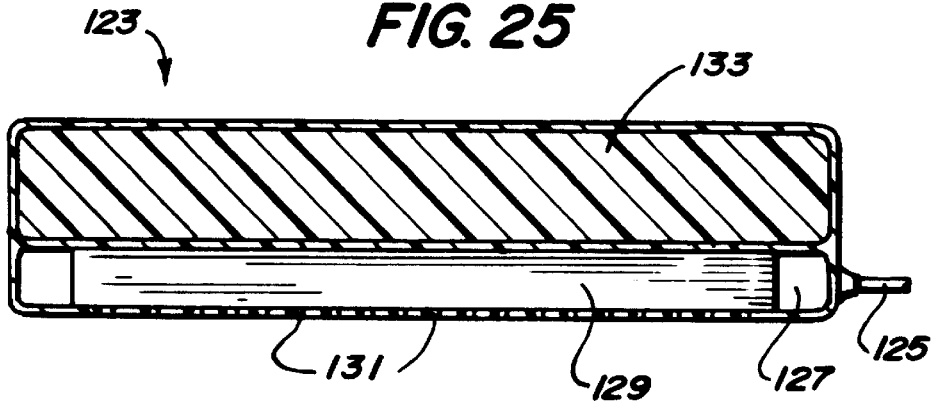
FIG. 25 is a transverse section through an embodiment of the invention incorporating a foam-type pad on the upper surface.

FIG. 25 shows a further embodiment of the invention in which there is a plenum chamber 122 below provided with transverse partition members 129 which prevent such plenum chamber from ballooning, and orifices 131 which provide an air film to provide a lubricating film of air to facilitate movement of the transfer apparatus, but instead of there being an upper separate air chamber, there is instead a foam rubber-type filler 133 or mattress inserted into the upper chamber. This type of transfer apparatus is made particularly for use in ambulances and the like where the patient will normally be placed immediately upon the transfer apparatus already upon a stretcher, and then transported to a hospital facility, and transferred directly to a gurney or even a bed, and it is convenient to have the transfer apparatus already, in effect, preinflated. As in the other embodiments the lower plenum is provided with an expanded peripheral chamber 127 extending partially up into the foam filed section 133 in order to provide the additional peripheral chamber capacity to facilities immediate or rapid inflation and deflation. Since the upper chamber is foam filled, there is usually sufficient give to it so the patient sinks into it and there is little chance that a patient will roll off. In addition, the extension of the inflated chamber 127 upwardly into the sides of the upper foam section tends to stiffen the sides during actual transfer or transport of the patient from one facility to another decreasing the chance of a patient rolling off the top. In addition, if desired the sides of the foam filled section itself could be raised or have raised sections further limiting possible rolling. The additional stiffness near the sides or edges when the lower chamber is inflated, however, tendering to stiffen the sides of the foam pad, is generally more effective in preventing rolling of the patient from the transfer device during actual use then actual foam extensions arranged on top. No low air loss chamber is provided for on top of the transfer apparatus of FIG. 25, because the use of low air loss equipment is essentially a fairly long-term treatment option and the transfer device of FIG. 25 is made essentially for ambulances and other short-term uses. Only one air inlet 125 is, therefore, necessary.

Figure 26:
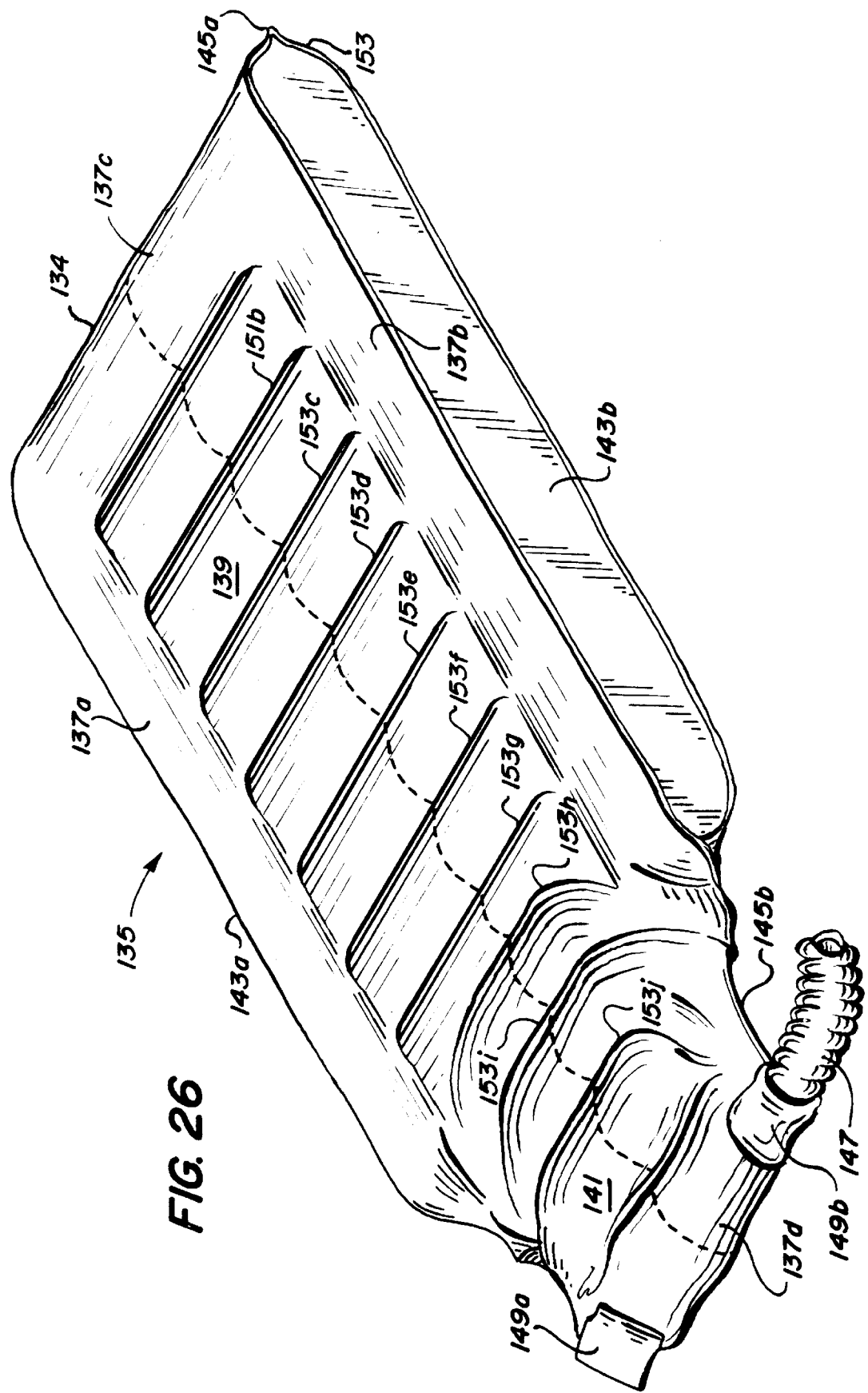
FIG. 26 is an isometric top view of a presently used commercial version of the invention similar to that for which the upper and lower surface sheets are shown in FIGS. 19 and 20.

FIG. 26 is an isometric view from the top of an alternative embodiment of the invention described generally above as in actual use, in which the peripheral walls or peripheral bands are provided only along the sides providing a pair of enlarged peripheral chambers 137a and 137b on each side bordered by an essentially flat perimeter wall band 143b and 143a (the latter band not being visible) and a further enlarged peripheral chamber 137c at the head end where the end of the top sheet 139 and bottom sheet 153 are sewn together in a seam 145a, the distance from such seam 145a and a first transverse partition member, not visible, but sewn to the top sheet 139 along the seam 151a, being, as shown, sufficiently greater than the distances between consecutive seams 151b, 151c, 151d, etc. to supply a significantly more capacious outer top chamber 137c generally equivalent to the cross section of the peripheral chambers 137a and 137b forming a large chamber around the perimeter of the apparatus. At the foot end of the transfer apparatus the top sheet 139 and bottom sheet 153 are again sewn together beyond the end of the perimeter bands 143a and 143b, with the inlet hose 147 entering air supply socks, not shown, housed within the end of the inflatable apparatus just within or behind the seam between the top and bottom sheets 139 and 153. The large peripheral chambers 137a and 137b then are, in effect, continued by the lowermost transverse chambers and the last section of the inflated structure 141 beyond the last transverse partition member under the last or lowermost sew line 153j, the result being that there is a large or capacious peripheral chamber or high air capacity chamber entirely around the outside of the transfer apparatus even though the lower end of the transfer apparatus has a decreasing overall width as seen in FIG. 26. Flaps 149a and 149b provide snap covers over the hose ends which covers each snap fitting, not shown, which intersnappingly fastens with a matching snap on the fitting on the end of the hose to hold such hose in place.

As will be recognized, the invention provides an improved inflatable transfer apparatus having an improved air flow around the apparatus and access to transverse central air chambers, while decreasing or essentially eliminating confusing x-ray or radiation shadows in medical radiology diagnostic imaging. The apparatus provides, in some embodiments, special inflatable so-called "log-rolling" chambers on top, and in other embodiments improved low air loss arrangements. The improved arrangement of peripheral chambers not only provides more security for the patient, but also provides very much improved air distribution which not only increases the efficiency and uniformity of initial inflation, but also facilitates emergency deflation to allow emergency cardiopulmonary resuscitation.

While the present invention has been described at some length and with some particularity with respect to several described embodiments, it is not intended that it should be limited to any such particulars or embodiments or the particular embodiment, but is to be construed broadly with reference to the appended claims so as to provide the broadest possible interpretation of such claims in view of the prior art and, therefore, to effectively encompass the intended scope of the invention.

I claim:

1. An improved inflatable medical patient transfer apparatus comprising:
   (a) a top sheet substantially rectangular in configuration, and having a longer and a shorter dimension including longer and shorter outer edges,
   (b) a bottom sheet having a similar configuration as the top sheet including a longer and shorter dimension and longer and shorter edges and perforated with a plurality of small orifices,
   (c) the top sheet having the same or somewhat greater dimensions than the bottom sheet,
   (d) a perimeter wall member connecting at least portions of the longer edges of the top and bottom sheets to each other,
   (e) a series of transverse partition members having shorter and longer edges said partition members being arranged substantially parallel to each other and transverse to the longer dimensions of the top and bottom sheets to define a substantially rectangular array of chambers in a central position with respect to the top and bottom sheets, the shorter outer edges of the transverse partition members being spaced from the perimeter wall member and the longer edges of the transverse partition members being secured the upper and lower edges of the transverse partition members to the top and bottom sheets, such perimeter wall member having a greater height than the height of such transverse partition members in an inflated condition of the transfer apparatus at least in a central portion of the transfer apparatus opposite the ends of adjacent chambers between transverse partition members underlying the main body portion of a patient supported upon the inflatable transfer apparatus, whereby an outside portion of the transfer apparatus is higher than the central portion at least opposite the transverse partition members and adjacent chambers underlying a patient.

2. An improved inflatable transfer apparatus in accordance with claim 1 wherein the perimeter wall member is of a greater height than the transverse partition member along substantially the entire longer outer edges of the top and bottom sheets of the transfer apparatus.

3. An improved inflatable transfer apparatus in accordance with claim 2 wherein the perimeter wall member extends around the entire perimeter of the transfer apparatus and is of greater height than the height of the transverse partition members thereby providing an expanded peripheral chamber about the entire perimeter of the apparatus.

4. An improved inflatable transfer apparatus in accordance with claim 1 additionally comprising:
(e) two separately inflatable chambers disposed upon the top sheet arranged parallel to the longer dimension of the top sheet of the transfer apparatus and adjacent to each other along the center of the top sheet.

5. An improved inflatable transfer apparatus in accordance with claim 3 additionally comprising:
(e) two separately inflatable chambers disposed upon the top of the top sheet arranged parallel to the longer dimension of the top sheet of the transfer apparatus and adjacent to each other along the center of the top sheet.

6. An improved inflatable transfer apparatus in accordance with claim 3 additionally comprising:
(e) a quick opening emergency valve in a wall of the peripheral chamber for exhaustion of air from said peripheral chamber to attain emergency deflation of the chambers between the transverse partition members.

7. An improved inflatable transfer apparatus in accordance with claim 4 additionally comprising:
(f) a separate lower plenum chamber provided at the bottom of the transfer apparatus formed by providing an intermediate substantially imperforate sheet between the top sheet and the perforated bottom sheet to separate the transfer apparatus into separate upper and lower chambers.

8. An improved inflatable transfer apparatus in accordance with claim 2 wherein the top of the transfer apparatus is composed of one color shade cloth and the bottom of a contrasting color shade cloth whereby proper placement of the inflatable apparatus upon a surface in uninflated condition with the top sheet designed for patient support oriented upwardly is facilitated.

9. An improved inflatable transfer apparatus in accordance with claim 2 wherein there is an indicia line down the center of the top of the transfer apparatus whereby rapid correct placement of a patient upon the inflatable transfer apparatus is facilitated.

10. An improved inflatable transfer apparatus in accordance with claim 8 wherein the top of the transfer apparatus is composed of dark colored cloth and the bottom of such apparatus of light colored cloth.

11. An improved inflatable transfer apparatus in accordance with claim 8 wherein there is an indicia line down the center of the top of the transfer apparatus whereby rapid correct placement of a patient upon the inflatable transfer apparatus is facilitated.

12. An air inlet arrangement for an inflatable medical patient transfer apparatus comprising:
(a) at least one inflatable chamber between a top sheet and a bottom sheet, said chamber being at least partially divided into a plurality of at least partially walled off sections by a plurality of partition members attached to the top and bottom sheets,
(b) at least two flexible cloth socks or tubes sewn into an end of the inflatable chamber of such transfer apparatus,
(c) such flexible cloth tubes each having an inlet orifice at an end of said tube, and
(d) at least two differentially sized outlet orifices in the aide of the flexible cloth tubes facing inwardly to the inflatable chamber of the transfer apparatus, the smaller of the outlets being substantially near the inlet orifice and the larger of the outlets being at the opposite end of the tube adjacent the opposite side of the inflatable chamber of the transfer apparatus.

13. A medical patient transfer apparatus comprising:
(a) a plurality of inflatable chambers each being defined between an upper sheet and a lower sheet and an outer peripheral wall connected to the outer edges of the upper and lower sheets,
(b) a top chamber being a low air loss chamber,
(c) a bottom chamber being a lower support chamber,
(d) at least one intermediate chamber incorporating an internally defined large peripheral chamber,
(e) means to separately inflate the chambers,
(f) wherein each of the chambers is constructed in the same manner with a series of spaced transverse partition members each having upper and lower longer edges and shorter ends, the upper and lower edges being attached to the upper and lower sheets and the shorter ends, being spaced from the outer peripheral wall thereby forming a series of adjacent chambers with open ends, the space between the ends of the transverse partition members and the outer peripheral wall together with a space between the transverse partition members and the peripheral wall at the end of the apparatus forming, an open peripheral chamber extending around the outside of the inflatable chambers internally of a perimeter wall with no substantial obstruction.

14. A medical patient transfer apparatus in accordance with claim 3 additionally comprising:
(e) an upper foam pad positioned above the top sheet,
(f) the space between the top and bottom sheets forming a lower plenum chamber with bottom air orifices,
(g) the expanded peripheral chamber partially extending into the lower side portions of the upper foam pad,
(h) means to inflate the lower chamber.

15. An inflatable transfer apparatus in accordance with claim 1 wherein the top sheet is of somewhat larger dimension than the bottom sheet at least at locations along the edge at which the the perimeter wall is of greater height than the transverse partition members to compensate for an upward curve of the top sheet at such locations.

16. An inflatable transfer apparatus in accordance with claim 3 wherein the top sheet is of somewhat larger dimensions than the bottom sheet to compensate for upward curve of the edges of the top sheet.

17. An inflatable transfer apparatus in accordance with claim 15 wherein the upper ends of at least some of the transverse partition members are upwardly oriented toward the top of the perimeter wall to obtain an extended attachment line with the top sheet of greater strength than a substantial point attachment.

18. An inflatable transfer apparatus in accordance with claim 16 wherein the upper ends of at least some of the transverse partition members are upwardly oriented toward the top of the perimeter wall to obtain an extended attachment line with the top sheet of greater strength than a substantial point attachment.

19. An improved inflatable transfer apparatus in accordance with claim 7 additionally comprising:
(g) differential valve means for directing air from a pneumatic pump separately into:

(i) a main body portion of the transfer apparatus comprising the spaces between the transverse partition members plus the expanded peripheral chamber about the periphery of the inflatable transfer apparatus, (ii) the bottom chamber, and (iii) either one of the two separately inflatable top chambers.

20. An improved inflatable transfer apparatus in accordance with claim 1 wherein the perimeter wall member extends between and connects the edges of the top and bottom sheets less than completely about the the longer and shorter edges of the top and bottom sheets.

21. An improved inflatable transfer apparatus in accordance with claim 20 wherein the perimeter wall member extends along at least a major portion of both longer edges of the top and bottom sheets.

22. An improved inflatable transfer apparatus in accordance with claim 21 wherein the perimeter wall is in two sections disposed along major portions of both longer edges of the top and bottom sheets.

23. An improved inflatable transfer apparatus in accordance with claim 22 wherein a substantial portion of both sections of perimeter wall along both longer edges of the transfer apparatus are of greater height than the height of the transverse partition members thereby providing an expanded peripheral chamber along these outer sections of the apparatus.

24. An improved inflatable transfer apparatus in accordance with claim 1 wherein the perimeter wall member extends about and connects together the longer and shorter outer edges of the top and bottom sheets.

25. An improved inflatable transfer apparatus in accordance with claim 24 wherein at least the sections of perimeter member along the longer edges of the top and bottom sheets are of greater height than the height of the transverse partition members.

26. An improved inflatable transfer apparatus in accordance with claim 1 wherein the transverse partition members are secured to the top and bottom sheets at points longitudinally displaced from each other along the longer dimension of the top and bottom sheets such that the transverse partition members are disposed at an angle with respect to perpendicular to the top and bottom sheets within the inflatable transfer apparatus during inflation of such apparatus.

27. An improved inflatable transfer apparatus in accordance with claim 26 wherein the transverse partition members lie substantially free of each other without overlapping between the top and bottom sheets when the transfer apparatus is deflated.

28. An improved inflatable transfer apparatus in accordance with claim 1 additionally comprising:

(e) a separate lower plenum chamber provided at the bottom of the transfer apparatus formed by providing an intermediate substantially imperforate sheet between the top sheet and the perforated bottom sheet to separate the apparatus into separate upper and lower chambers.

29. An improved inflatable transfer apparatus in accordance with claim 1 additionally comprising:

(e) two separately inflatable chambers disposed upon the top of the top sheet arranged along the longer dimension of the top sheet of the transfer apparatus and adjacent to each other along the center of the top sheet parallel to the longer sides.

30. An improved inflatable transfer apparatus in accordance with claim 24 additionally comprising:

(e) a quick opening emergency valve in the wall of the expanded peripheral chamber along the shorter and longer edges of the top and bottom sheets for exhaustion of air from said peripheral chamber to attain emergency deflation of the chambers between the transverse partition members.

31. An improved inflatable transfer apparatus in accordance with claim 2 wherein the transverse partition members and the array of transverse chambers underlying a portion of the top sheet adapted to support a trunk or torso portion of a patient have substantially uniform dimensions top to bottom from one end to the other transversely across the mat.

32. An improved inflatable transfer apparatus in accordance with claim 31 wherein transverse partition members and the array of transverse chambers underlying the portion of the top sheet adapted to support a leg portion of a patient has a lesser height in the central portions of the transverse partition members than at the ends of such partition members.

33. An improved inflatable transfer apparatus in accordance with claim 32 wherein the upper ends of at least some of the transverse partition members are upwardly oriented toward the top of the perimeter band to obtain an extended attachment line with the top sheet of greater strength than a substantial point attachment.

34. An inflatable medical patient transfer apparatus comprising:

(a) top and bottom sheets having an elongated configuration of suitable dimensions to completely underlie a human form, said top and bottom sheets having longitudinal and transverse edge portions, (b) a perimeter band member extending between and contacting at least a substantial extent of the longitudinal edge portions of said top and bottom sheets and secured to as well as securing together said top and bottom sheets, (c) a series of transverse partition members having upper and lower edges as well as outer ends disposed at least along a central portion of the transfer apparatus at spaced intervals forming a series of open ended chambers between the top and bottom sheets to which the upper and lower edges of the transverse partition members are at least partially attached, the outer ends of the transverse partition members and the chambers defined therebetween being spaced from the perimeter band member, and (d) the height of the perimeter band member being greater than the height of the outer ends of the transverse partition members opposite the outer ends of such partition members in an inflated condition of the transfer apparatus, whereby an expanded peripheral chamber is formed between the top and bottom sheets at least opposite the ends of the transverse partition members underlying the body of a patient upon the apparatus.

35. An inflatable medical patient transfer apparatus in accordance with claim 34 wherein the perimeter band is from five to seven inches in height in the portion of the perimeter band member that is greater than the height of the transverse partition members which members are from four to six inches in height in their major portion.

36. An inflatable medical patient transfer apparatus in accordance with claim 35 wherein the height of the perimeter band member is from one inch to two inches higher than the height of the transverse partition members in their major portion.

37. An inflatable transfer apparatus in accordance with claim 34 wherein the top sheet is of somewhat larger dimension to compensate for upward curve of the edges of the top sheet.

38. An inflatable transfer apparatus in accordance with claim 36 wherein the top sheet is of somewhat larger dimension than the bottom sheet as portions wherein the perimeter wall is of greater height than the transverse partition members to compensate fo the upward curve of the top sheet at such location.

39. An inflatable transfer apparatus in accordance with claim 34 wherein the ends of at least some of the transverse partition members are upwardly oriented toward the top of the perimeter band to obtain an extended attachment line with the top sheet than a substantial point attachement.

40. An inflatable transfer apparatus in accordance with claim 36 wherein the ends of at least some of the transverse partition members are upwardly oriented toward the top of the perimeter band to obtain an extended attachment line with the top sheet greater than a substantial point attachment.

41. An improved inflatable transfer apparatus in accordance with claim 40 wherein in addition transverse partition members forming an array of transverse chambers underlying a portion of the top sheet adapted to support a leg portion of a patient has a lesser height in the central portions of the transverse partition members than at the ends of such partition members.

* * * * *